(12) United States Patent
Tomizawa et al.

(10) Patent No.: US 8,841,508 B2
(45) Date of Patent: Sep. 23, 2014

(54) NON-HUMAN MAMMALIAN ANIMAL MODEL FOR TYPE 2 DIABETES

(75) Inventors: Kazuhito Tomizawa, Kumamoto (JP); Fanyan Wei, Kumamoto (JP)

(73) Assignees: National University Corporation, Kumamoto-Shi (JP); Kumamoto University, Kumamoto-Shi (JP)

( * ) Notice: Subject to any disclaimer, the term of this patent is extended or adjusted under 35 U.S.C. 154(b) by 0 days.

(21) Appl. No.: 13/509,228

(22) PCT Filed: Nov. 10, 2010

(86) PCT No.: PCT/JP2010/070006
§ 371 (c)(1),
(2), (4) Date: May 10, 2012

(87) PCT Pub. No.: WO2011/058994
PCT Pub. Date: May 19, 2011

(65) Prior Publication Data
US 2012/0233714 A1 Sep. 13, 2012

(30) Foreign Application Priority Data

Nov. 11, 2009 (JP) .................................. 2009-258382
Aug. 12, 2010 (JP) .................................. 2010-181161

(51) Int. Cl.
*A01K 67/027* (2006.01)
*C12N 15/09* (2006.01)

(52) U.S. Cl.
USPC .................. 800/18; 800/3; 800/21; 800/9

(58) Field of Classification Search
CPC ............... A01K 2227/105; A01K 2267/0387; A01K 67/0275; A01K 67/0276
USPC .............................................. 800/18, 3, 21, 9
See application file for complete search history.

(56) References Cited

U.S. PATENT DOCUMENTS 5,464,764 A * 11/1995 Capecchi et al. ............ 435/6.14
2006/0021072 A1   1/2006 Matsushima

FOREIGN PATENT DOCUMENTS

JP         2006-34132 A    2/2006

OTHER PUBLICATIONS

Tomizawa, Igaku no Ayumi, 2008, 226:245-246.*
Tomizawa, Protein nucleic acid and enzyme, 2009, 54:808-812.*
Kulkarni et al, Cell, 1999, 96:329-339.*
Leibiger et al, Annu Rev Nutr, 2008, 28:233-251.*
Stancakova et al, J Clin Endocrinol Metab, 2008, 93:1924-1930.*
Gama Sosa et al, Brain Struct Funct, 2009, 214:91-109.*
Clark et al, Nature Reviews: Genetics, 2003, 825-833.*
Niemann et al, Rev Sci Tech Off Int Epiz, 2005, 24:285-298.*
Wheeler et al, Theriogenology, 2001, 56:1345-1369.*
Prelle et al, Anatomia Histologia Embryologia, 2002, 31:169-186.*
Moreadith et al, J Mol Med, 1997, 75:208-216.*
Mullins, Nature, 1990, 344:541-544.*
Hammer et al, Cell, 1990, 63:1099-1112.*
Mullins et al, 1989, EMBO, 8:4065-4072.*
Taurog, 1988, J. Immunology, 141:4020-4023.*
Qi et al, Hypertension, 2005, 45:1004-1011.*
Steinthorsdottir et al, Nature Genetics, 2007, 39:770-775.*
GenBank Accession No. NC_000079, Jul. 12, 2007.*
Horikoshi et al., "Variations in the HHEX gene are associated with increased risk of type 2 diabetes in the Japanese population," Diabetologia, vol. 50, 2007, pp. 2461-2466.
International Search Report issued in PCT/JP2010/070006, mailed on Dec. 14, 2010.
Scott et al., "A Genome-Wide Association Study of Type 2 Diabetes in Finns Detects Multiple Susceptibility Variants," Science, vol. 316, Jun. 1, 2007, pp. 1341-1345.
Steinthorsdottir et al., "Abstract 2318: The Type 2 Diabetes Gene CDKAL1 Discovered by Genome-wide Association is Expressed in Beta Cells and Modulated by Glucose Concentration," Circulation, 2007.
Tartaglia et al., "Identification and Expression Cloning of a Leptin Receptor, OB-R," Cell, vol. 83, Dec. 29, 1995, pp. 1263-1271.
Tomizawa, "Cdk5 and risk of type 2 diabetes," Igaku no ayumi, vol. 226, No. 3, Jul. 19, 2008, pp. 245-246.
Tomizawa, "Functions of Cdk5 in non-neuronal tissues: Focusing on regulation of insulin secretion," Proteins, Nucleic Acids & Enzymes, vol. 54, No. 7, Jun. 1, 2009, pp. 808-812.
Tomizawa, "tRNA Modification & Development of Type 2 Diabetes Mellitus," Abstract of 12th RNA Meeting in Tokyo, SP-2, Jul. 27, 2010, p. 4. Zhang et al., "Positional cloning of the mouse obese gene and its human homologue," Nature, vol. 372, Dec. 1, 1994, pp. 425-432.

* cited by examiner

*Primary Examiner* — Valarie Bertoglio
*Assistant Examiner* — Chi-Feng Hsu
(74) *Attorney, Agent, or Firm* — Birch, Stewart, Kolasch & Birch, LLP.

(57) ABSTRACT

The present invention provides a non-human mammalian animal model for type 2 diabetes, which spontaneously develops a pathological condition similar to human type 2 diabetes of a non-obese type seen in some Japanese people. The non-human mammalian animal model for type 2 diabetes according to the present invention is deficient in a Cdkal1 gene function on the chromosome of the β cell of the pancreas. More specifically, the non-human mammalian animal model for type 2 diabetes may be produced by interbreeding a non-human mammal carrying a site-specific recombination enzyme recognition sequence in the 3'-untranslated region and the 5'-untranslated region of a particular domain carrying one exon or more exons of the Cdkal1 gene with a non-human mammal in which a gene of a site-specific recombination enzyme capable of recognizing the site-specific recombination enzyme recognition sequence and splicing out the particular domain is inserted in such a manner as expressing specifically at a site downstream of a promoter of a gene expressing specifically in the pancreas.

7 Claims, 9 Drawing Sheets

THE STRUCTURE OF Cdkal1 GENE

NON-HUMAN MAMMALIAN ANIMAL MODEL FOR TYPE 2 DIABETES

CROSS-REFERENCE TO RELATED APPLICATIONS

This application claims the benefit of PCT/JP2010/070006, filed on Nov. 10, 2010, and of foreign applications JAPAN 2010-181161, filed on Aug. 12, 2010, and JAPAN 2009-258382, filed on Nov. 11, 2010.

TECHNICAL FIELD

The present invention relates to a non-human mammalian animal model for type 2 diabetes, which is deficient in a Cdkal1 gene function, and to a screening method for screening a preventive or therapeutic agent for the type 2 diabetes using the non-human mammalian animal model for type 2 diabetes.

BACKGROUND TECHNOLOGY

Hitherto, the diabetes is known as a disease that is caused by a morbid abnormal elevation of the blood glucose level due to the defects of the glucose metabolism, resulting in various complications.

In particular, the type 2 diabetes caused by a decreased insulin secretion and a reduced susceptibility to insulin is considered as accounting for a majority of total patients with diabetes in this country. And it is a complicated multifactorial disease that develops and advances by a variety of environmental factors including overeating, dietary composition, stress, lack of exercise, and the like, in addition to the genetic causes.

To date, therefore, many researchers have conducted research on type 2 diabetes using non-human mammalian animals which are considered to demonstrate pathological conditions of the type 2 diabetes.

As such non-human mammalian animals, there may be mentioned, for example, ob/ob mice or db/db mice, discovered by Jackson Research Laboratory, U.S.

These mice may cause a decrease in the energy consumption in addition to an increase in the energy intake due to overeating, and demonstrate phenotypes including, for example, high blood glucose, hyperinsulinemia, insulin resistance, a weight increase in the white adipocytes, and so on.

In 1994, the corresponding disease gene of the ob/ob mouse was identified by positional cloning and designated as "leptin" (see, for example, Non-Patent Literature Document #1). And, in 1995, the gene for leptin receptor was cloned and revealed as the disease gene for the db/db mouse (see, for example, Non-Patent Literature Document #2). At the present time, both of these mice have been used extensively as animal models for diabetes and obesity in biomedical research including the physiological and pharmacological functions of leptin.

Research on applications of animals developed by these genetic engineering techniques are expected to help not only in making a detailed clarification of a molecular function of the secretion and action of insulin, but also in making it feasible to clarify the pathological conditions of the type 2 diabetes as a multifactorial disease by the load of several genetic factors and environmental factors. Further, this research field is considered as indispensable to an application to development of new treatment methods including gene therapy, regenerative therapy and therapeutic agents as well as to a clarification of the onset and the pathological conditions of the diabetes.

PRIOR ART DOCUMENTS

[Non-Patent Literature Document #1] Zhang Y et al., Nature 1994; 372(6505):425-432
[Non-Patent Literature Document #2] Tartaglia L A. et al., Cell 1995; 83(7): 1263-1271

SUMMARY OF THE INVENTION

Problems to be Solved by the Invention

Because non-human mammalian animals such as ob/ob mice or db/db mice develop severe obesity, it is difficult to state that these non-human mammalian animals represent the pathological conditions of type 2 diabetes patients unaccompanied by obesity.

That is to say, diabetic patients having a mutation in leptin or its receptor is extremely rare so that those non-human mammalian animals are not always appropriate for general research on type 2 diabetes.

Other non-human mammalian animals such as KK mice or Ay mice are also used for research on type 2 diabetes, however, some difficulties are encountered in using those non-human mammalian animals for practical research on type 2 diabetes because they may have obesity and their disease genes are not found yet.

The present invention has been made with the above situation taken into account, with the objective of providing a novel non-human mammalian animal model for type 2 diabetes which spontaneously develops a pathological condition similar to type 2 diabetes of a non-obese type seen in some Japanese people.

The present invention has another object, which is to provide a process for using the non-human mammalian animal model for type 2 diabetes, and a screening method for screening a preventive or therapeutic agent for type 2 diabetes that may be caused by defects of Cdkal1 gene.

Means to Solve the Problems

In order to achieve the above objects, the present invention as claimed in claim 1 provides a non-human mammalian animal model for type 2 diabetes, which is deficient in a Cdkal1 gene function specifically on the chromosome of β cells of the pancreas.

The present invention as claimed in claim 2 provides the non-human mammalian animal model for type 2 diabetes as claimed in claim 1, which is produced by interbreeding a non-human mammal carrying a site-specific recombination enzyme recognition sequence on a 3'-untranslated region and a 5'-untranslated region of a particular domain including one exon or or more exons of the Cdkal1 gene with a non-human mammal carrying a gene for a site-specific recombination enzyme capable of recognizing the above site-specific recombination enzyme recognition sequence and splicing out the above particular domain inserted into a site downstream of a promoter for a gene expressing specifically in the pancreas.

The present invention as claimed in claim 3 is characterized in that the particular domain of the type 2 diabetes non-human mammalian animal model as claimed in claim 2 carries at least exon 5. [0018]

The present invention as claimed in claim 4 is characterized in that the non-human mammalian animal model for type 2 diabetes comprises a rodent.

The present invention as claimed in claim 5 is characterized in that the rodent is a mouse.

The present invention as claimed in claim 6 provides a method for using a non-human animal deficient in a Cdkal1 gene function specifically on the chromosome of β cell of the pancreas as the non-human mammalian animal model for type 2 diabetes.

The present invention as claimed in claim 7 provides a screening method for screening a preventive or therapeutic agent for type 2 diabetes caused by defects of Cdkal1 gene by administering a test substance to the non-human mammalian animal model for type 2 diabetes deficient in a Cdkal1 gene function specifically on the chromosome of β cells of the pancreas and evaluating the degree of type 2 diabetes in the non-human mammalian animal model for type 2 diabetes.

The present invention as claimed in claim 8 is characterized by the screening method for screening the preventive or therapeutic agent for type 2 diabetes resulting from the defects of the Cdkal1 as claimed in claim 7, in which the test substance is administered to the non-human mammalian animal deficient in Cdkal1 gene function specifically on the chromosome of the β cell of the pancreas and to a wild type non-human mammalian animal and comparing both of the non-human mammalian animals to evaluate the degree of the type 2 diabetes in the non-human mammalian animal model for type 2 diabetes.

The present invention as claimed in claim 9 is characterized by a method for producing the non-human mammalian animal model for type 2 diabetes lacking the function of the Cdkal1 gene specifically on the chromosome of the β cell of the pancreas.

Effect of the Invention

The present invention as claimed in claim 1 can provide the new non-human mammalian animal model for type 2 diabetes that is deficient in a Cdkal1 gene function specifically on the chromosome of the β cells of the pancreas and that develops spontaneously a pathological condition similar to type 2 diabetes of non-obese type seen in some Japanese people.

The non-human mammalian animal model according to the present invention does not exert an influence on the expression of the Cdkal1 gene at a site other than the pancreas because the Cdkal1 gene of the non-human mammalian animal model is knocked out specifically to the organ in the pancreas. Therefore, in the event where the non-human mammalian animal model for type 2 diabetes, according to the present invention is used, for example, for tests or research, a comparative experiment can be carried out more accurately than an experiment using the wild type non-human mammalian animal as a control because a difference of the expression of the Cdkal1 gene at the site other than the pancreas is not needed to be taken into account when compared with the wild type non-human mammalian animal used as a control.

In accordance with the present invention as claimed in claim 2, the non-human mammalian animal model for type 2 diabetes is produced by interbreeding the non-human mammal carrying the site-specific recombination enzyme recognition sequence in the 3'-untranslated region and the 5'-untranslated region of the particular domain carrying one exon or more exons of the Cdkal1 gene with the non-human mammal carrying the gene of the site-specific recombination enzyme capable of recognizing the site-specific recombination enzyme recognition sequence and splicing out the particular domain inserted at a site downstream of the promoter of the gene expressing specifically in the pancreas, so that the expression of a normal Cdkal1 gene can be prevented by expressing the site-specific recombination enzyme in the pancreas in an organ-specific manner and splicing out the particular domain.

The present invention as claimed in claim 3 can more securely prevent the expression of the normal Cdkal1 gene in the pancreas in an organ-specific manner because the particular domain carries at least exon 5.

The present invention as claimed in claim 4 provides the non-human mammalian animal model for type 2 diabetes, which demonstrates the pathological condition of the type 2 diabetes although the non-human mammalian animal is the rodent to be used widely for experiments and the like.

The present invention as claimed in claim 5 provides the non-human mammalian animal model for type 2 diabetes, which demonstrates the pathological condition of the type 2 diabetes, because the rodent comprises a mouse which has been used widely for experiments or other similar purposes and which is recognized as a useful animal based on various findings.

The present invention as claimed in claim 6 provides a method for using the non-human mammalian animal as the non-human mammalian animal model for type 2 diabetes, comprising a process for using the non-human mammalian animal deficient in the Cdkal1 gene function specifically on the chromosome of the β cell of the pancreas as the non-human mammalian animal model for type 2 diabetes.

The present invention as claimed in claim 7 provides a screening method for screening the preventive or therapeutic agent for type 2 diabetes caused by the defects of the Cdkal1 gene, which comprises administering the test substance to the non-human mammalian animal model for type 2 diabetes deficient in the Cdkal1 gene function specifically on the chromosome of the β cells of the pancreas and evaluating the degree of type 2 diabetes in the non-human mammalian animal model for type 2 diabetes.

The present invention as claimed in claim 8 provides the screening method for screening the preventive or therapeutic agent for type 2 diabetes caused by the defects of the Cdkal1 gene, which comprises administering the test substance to the non-human mammal deficient in the Cdkal1 gene function specifically on the chromosome of the β cell of the pancreas and to the wild type non-human mammal and evaluating the pathological conditions of the type 2 diabetes developed in the deficient non-human mammalian animal based on a comparison with those of the wild type non-human mammalian animal.

The present invention as claimed in claim 9 provides a method for producing the new non-human mammalian animal model for type 2 diabetes developing spontaneously the pathological condition similar to the type 2 diabetes of a non-obese type popular in the Japanese people, comprising a method for producing the non-human mammalian animal model for type 2 diabetes deficient in the Cdkal1 gene function specifically on the chromosome of the β cell of the pancreas.

MODES FOR CARRYING OUT THE INVENTION

Figure 1:
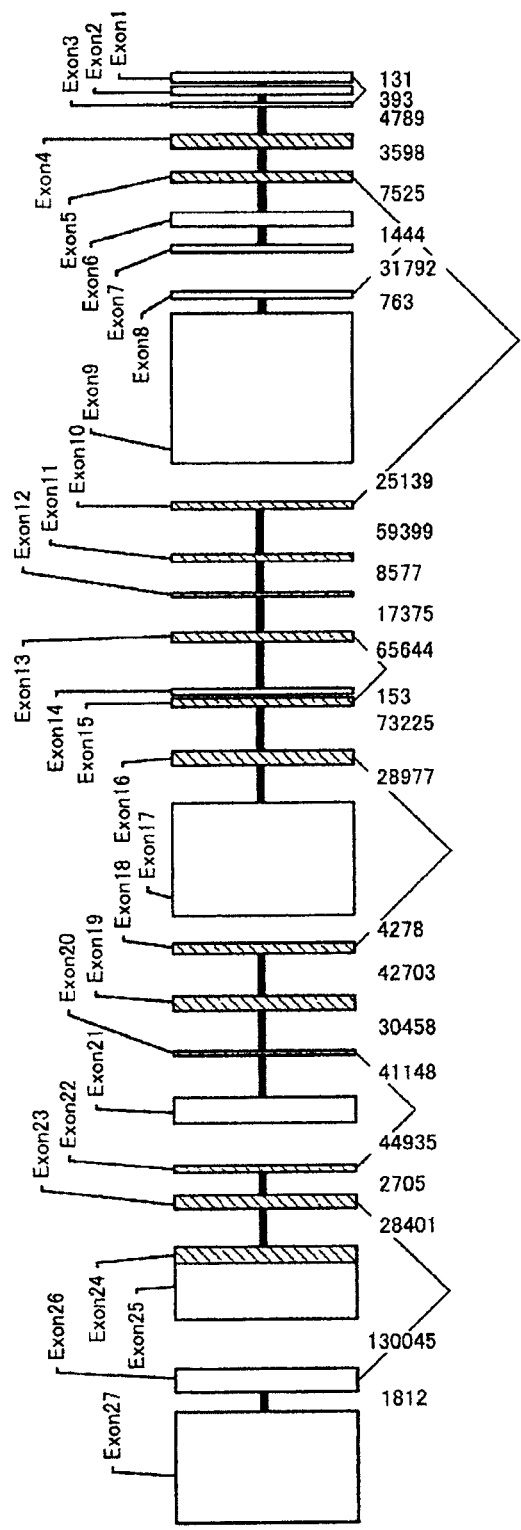
FIG. 1 An illustration showing the structure of the Cdkal1 gene.

The present invention provides the non-human mammalian animal model for type 2 diabetes, which is deficient in the Cdkal1 gene function specifically on the chromosome of the β cell of the pancreas.

Deficiency in a Cdkal1 gene function is a known risk factor of type 2 diabetes (see Science (2007) 316, 1331; Science (2007) 316, 1336; Science (2007) 316, 1341; Nat Genet (2007) 39, 770).

However, the function of the Cdkal1 from expression of the Cdkal1 gene is not yet clarified, and the association of the Cdkal1 gene with type 2 diabetes is still left unclear.

As a result of extensive research on the association of the Cdkal1 gene with type 2 diabetes, it has been found that persons having a specific mutation (a single nucleotide polymorphism: SNP) in the Cdkal1 gene region demonstrate a significantly reduced insulin secretion from the β cell of the pancreas compared with persons having no such specific mutation, leading to the likelihood to causing an easier development of type 2 diabetes on this basis.

More specifically, Cdkal1 is an enzyme modifying tRNA chemically and is supposed to demonstrate a function of facilitating the translation of insulin by modifying the tRNA.

Based on this new finding, the present inventors have now hit an idea of producing a knock-out non-human mammalian animal that is deficient in the Cdkal1 gene specifically to the β cell of the pancreas, and the present invention has been completed from this finding.

In working embodiments as will be described below, the non-human mammalian animal model for type 2 diabetes, which is deficient in a Cdkal1 gene function specifically on the chromosome of the β cell of the pancreas, is intended to mean a non-human mammalian animal that has lost its function of expressing Cdkal1 due to an inactivation of the endogenous gene encoding Cdkal1 in the β cell of the pancreas of the non-human mammalian animal by a genetic mutation including, for example, gene ablation, deletion, substitution, or the like.

As the non-human mammalian animal to be used for the present invention, there may be mentioned, for example, a rodent which may include, for example, a mouse, rat and so on, although it is not limited to a particular one. In other words, there may be used any non-human mammalian animal which carries an endogenous gene coding for Cdkal1 and which has been used conventionally for experiments.

The type 2 diabetes model non-human mammalian animal according to a working embodiment of the present invention may be produced by interbreeding the non-human mammal which carries a site-specific recombination enzyme recognition sequence in the 3'-untranslated region and the 5'-untranslated region of the particular domain containing one exon or more exons of the Cdkal1 gene with the non-human mammal in which the gene of the site-specific recombination enzyme capable of recognizing the site-specific recombination enzyme recognition sequence and splicing out the particular domain is inserted at a location downstream of the promoter for the enzyme expressing specifically in the pancreas.

In accordance with a working embodiment of the present invention, the site-specific recombination enzyme is intended to mean an enzyme that catalyzes a process of a site-specific mutation, that is, a process of mutation occurring at a particular intermolecular or intramolecular site of DNA. And the site-specific recombination enzyme recognition sequence is intended herein to mean a particular base sequence that can recognize a site-specific recombination enzyme. Moreover, the site-specific recombination enzyme may possess a function of splicing out a DNA fragment flanked by the recognition sequences and cycling it as well as carrying out the inverse reaction (including an insertion of a cyclic molecular through the recognition sequences).

In accordance with a working embodiment of the present invention, the site-specific recombination enzyme and the site-specific recombination enzyme recognition sequence may not be limited each to a particular one, and such an enzyme may include, for example, an FLP recombinase derived from *Saccharomyces cerevisiae* recognizing the FRT sequence, an enzyme R recognizing RS sequence in the R/RS system derived from *Zygosaccharomyces rouxii* (Onouchi H et al. (1995) Mol. Gen. Genet. 247, 653-660, Onouchi H et al. (1991) Nucl. Acids Res. 19, 6373-6378), an enzyme Cre recognizing lox (loxP) sequence in the Cre/lox (Cre/loxP) system derived from bacteriophage P1 (Albert H et al. (1995) Plant J. 7, 649-659, Liu Q et al. (1998) Current Biol. 8, 1300-1309, Abmemski K et al. (1983) Cell 32, 1301-1311), and so on.

The promoter to be located at a site upstream of the gene of the site-specific recombination enzyme is intended to include, but be not limited to, an insulin promoter, a PDX1 promoter, and any other promoter of a gene expressing specifically in the pancreas of the non-human mammalian animal model for the type 2 diabetes.

Further, non-human mammalian animal model for type 2 diabetes according to a working embodiment of the present invention may preferably contain the particular domain carrying at least exon 5 enclosed by two or more site-specific recombination enzyme recognition sequences, which may be spliced out by the site-specific recombination enzyme.

As shown in FIG. 1, the Cdkal1 gene carries 27 exons. In FIG. 1, the right-handed side is indicated as the 5'-side, and the left-handed side is indicated as the 3'-side. Moreover, in FIG. 1, the exon represented by outline characters indicates an exon that cannot be translated by splicing at least in the β cell. The numeral shown in FIG. 1 indicates a number of bases between each of the exons.

Among the exons contained in the Cdkal1 gene, it is obvious that exon 1 to exon 3 are each an exon which does not encode a protein as have been described above. Therefore, even if the exon 1 to exon 3 would have been deleted, the expression of Cdkal1 cannot be inhibited. On the other hand, exon 4 is known to be an exon encoding a protein, however, it is considered possible by the work done by the present inventors that an exon or exons located farther in the downstream region can be translated by a correct reading frame even if exon 4 would be deleted.

Moreover, even if an exon or exons located at a site from exon 6 and the following ones would be deleted, it is considered possible to interfere with the expression of Cdkal1. It is further considered feasible, however, that an appropriate splicing-out cannot be carried out because there is a limit to a length to be spliced out by the above site-specific recombination enzyme.

In addition, the possibility that a translated product may cause an expression of a Cdkal1-like function can be reduced as long as it would be located at the possible upstream site.

Therefore, it is possible that the expression of Cdkal1 can be suppressed for sure by deleting at least exon 5 of the Cdkal1 gene and, moreover, the particular domain can be spliced out favorably by the site-specific recombination enzyme, while the expression of such a Cdkal1-like function of the translated product can be inhibited.

As a result of glucose tolerance tests conducted by the inventors using the non-human mammalian animal model for type 2 diabetes (Cdkal1 knock-out mice) according to the present invention and wild type mice, a significantly higher blood glucose level was observed in the Cdkal1 knock-out mice than in the wild type mice, and an abnormality in the glucose tolerance function was observed in the Cdkal1 knock-out mice, as will be described in detail below. On the other hand, no increase in the body weight characteristic in type 1 diabetes was recognized in the Cdkal1 knock-out mice.

As described above, the non-human mammalian animal model for type 2 diabetes according to the present invention can reproduce the pathological conditions similar to those of the human type 2 diabetes extremely well.

In accordance with a working embodiment of the present invention, there is no particular limit as long as the screening method for screening the preventive or therapeutic agent for type 2 diabetes can evaluate a degree of type 2 diabetes of the above non-human mammalian animal by administering a test substance to the type 2 diabetes model non-human mammalian animal according to the working embodiment of the present invention. As the method for administration of the test substance, there may be mentioned various administration procedures including, but being not limited to, oral administration, intravenous administration, enteral administration, and so on.

As the method for evaluating the degree of type 2 diabetes, there may be mentioned, for example, a method for measuring a blood glucose level of the non-human mammalian animal at the time of fasting or at the time of glucose tolerance, or a method for measuring a concentration of glycosylated hemoglobin A (HbA1c) in the blood.

In order to evaluate the degree of type 2 diabetes, it is preferred that the test substance is administered to the non-human mammalian animal deficient in the Cdkal1 gene function specifically on the chromosome of the β cells of the pancreas and to the wild type non-human mammalian animal, resulting in comparing both of the non-human mammalian animals and evaluating them.

In accordance with a working embodiment of the present invention, the non-human mammalian animal of a wild type is intended to mean an animal that is allogeneic to the non-human mammalian animal deficient in a Cdkal1 gene function, and a litter of such animals is particularly preferred. As the non-human mammalian animal deficient in a Cdkal1 gene function, young mice born in accordance with the Mendel's laws are of a wild type in a litter of the Cdkal1-deficient type mice. These mice are preferred because they can be used for more accurate comparative tests. As described above, a preferred specific example of the non-human mammalian animal model for type 2 diabetes for the Cdkal1 gene may include Cdkal1 knock-out mice. As the wild type mice, there may be mentioned specifically wild type mice which are a litter of the above knock-out mice.

As described above, the screening method for screening the preventive or therapeutic agent for type 2 diabetes can contribute to the development of a therapeutic agent for diabetes.

Further, the method for producing the type 2 diabetes model non-human mammalian animal according to a working embodiment of the present invention comprises deleting a function of the Cdkal1 gene specifically on the chromosome of the β cells of the pancreas of the non-human mammalian animal.

Although the non-human mammalian animal to be used for the production method is not limited to a particular one, it is preferred that the non-human mammalian animals to be used for general experiments are of a definite line. For instance, it might be possible to form type 2 diabetes model non-human mammalian animals from wild animals in accordance with the production method of a working embodiment of the present invention, however, for using research on type 2 diabetes and screening the preventive or therapeutic agent, it is preferred to use non-human mammalian animals having a definite bloodline because wild animals may have genetically unclear portions or are unknown in bloodline in various respects.

The following is a more specific description of the non-human mammalian animal model for type 2 diabetes according to the present invention by way of working examples in accordance with the order of production processes by taking a mouse as an example of the non-human mammalian animal for brevity of explanation.

(Preparation of Targeting Vector)

Figure 2:
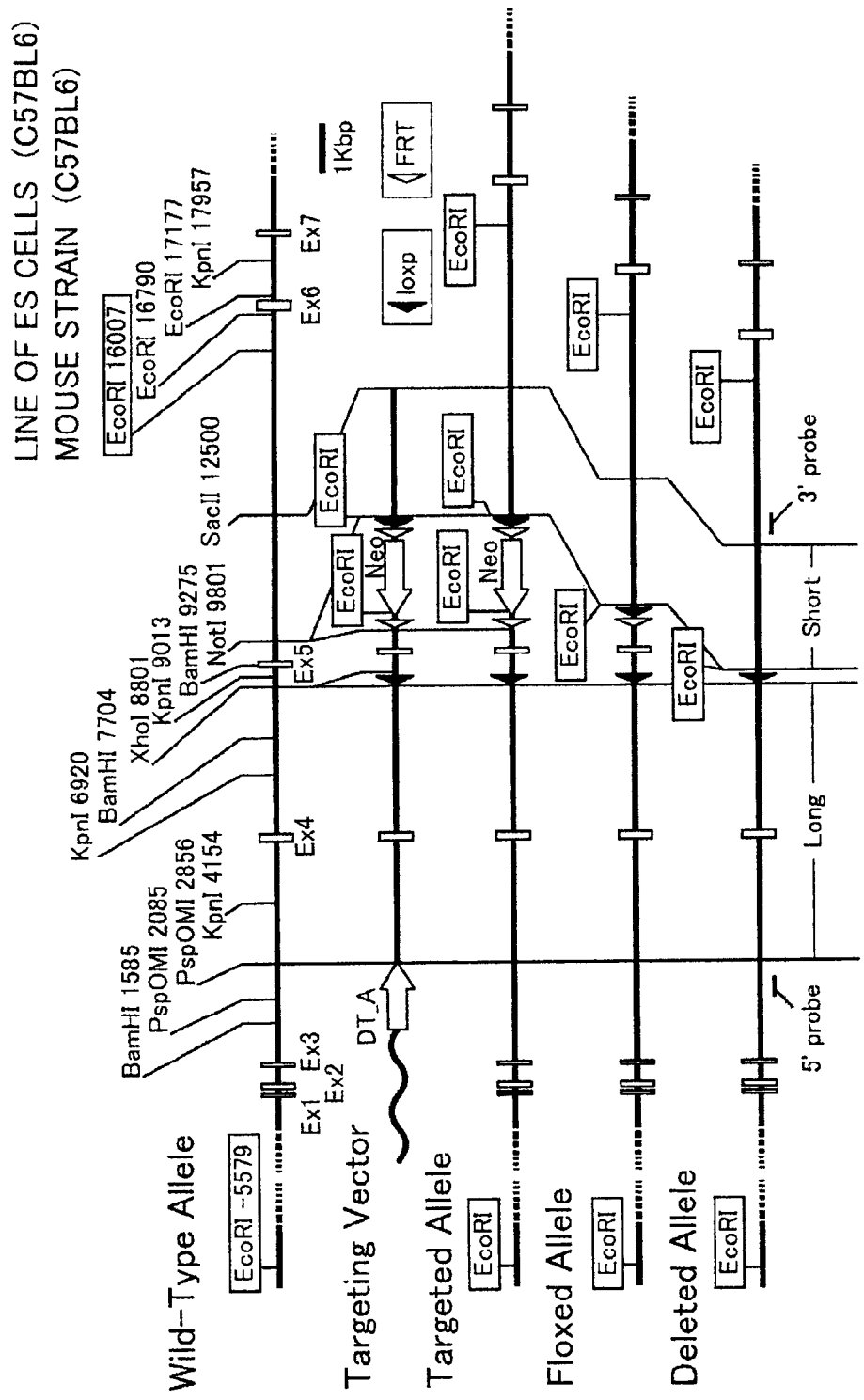
FIG. 2 An illustration showing a concept for producing the non-human mammalian animal model for type 2 diabetes according to the working embodiment of the present invention.

A targeting vector to be used for the following working examples was formed on the basis of the strategy as indicated in FIG. 2.

Specifically, firstly, a PCR product of a Cdkal1 fragment (2856-8800) (SQ ID NO:1) was obtained from a Bac clone and subcloned in pBSIISK using a restriction enzyme site as follows:

PspOMI-Cdkal1(2856-8800)–XhoI (1)

Next, a PCR product carrying a loxP sequence (SQ ID NO:3) at the 5'-upstream side of the Cdkal fraction (8801-9800) (SQ ID NO:2) was obtained from a Bac clone using primers designed each so as to contain a loxP sequence, and then subcloned in pBSIISK using a restriction enzyme as follows:

XhoI-loxP-Cdkal1(8801-9800)–NotI (2)

NotI-Cdkal1(9801-12500)–SacII (3)

Then, a PCR product carrying a loxP sequence at the 3'-downstream side of the Cdkal1 fraction (9801-12500) (SQ ID NO:4) was obtained from a Bac clone using primers designed so as to contain a loxP sequence, and then subcloned in pBSIISK using a restriction enzyme as follows:

NotI-Cdkal1(9801-12500)–SacII            (4)

Thereafter, the Cdkal1 fraction (3) was inserted into a vector (pBS-FRT-Neor-FRT-loxP) which was separatedly formed so as to contain Neomycin resistance gene (SQ ID NO:5) and FRT sequence (SQ ID NO;6) as follows:
Vector: pBS-FRT-Neor-FRT-loxP NotI-SacII digest
Insert: pBSIISK+Cdkal1(9801-12500) NotI-SacII digest
Construct1: pBS-FRT-Neor-FRT-loxP-Cdkal1(9801-12500)

The Cdkal1 fraction (1) was then linked to the Cdkal1 fraction (2) as follows:
Vector: pBSIISK+Cdkal1(2856-8800) XhoI-NotI digest
Insert: pBSIISK+loxP-Cdkal1(8801-9800) XhoI-NotI digest
Construct2: pBSIISK+Cdkal1(2856-8800)-loxP-Cdkal1(8801-9800)

Thereafter, a diphtheria toxin fragment (DTA) (SQ ID NO:7) was inserted into Construct 2 as a negative selection marker in the manner as will be described below.
Vector: Construct2 PspOMI digest
Insert: pBS-DTA NotI-PspOMI digest
Construct3: pBSIISK+DTA-Cdkal1(2856-8800)-loxP-Cdkal1(8801-9800)

A complete targeting vector (SQ ID NO:8) was then constructed in the manner as follows:
Vector: Construct3 NotI-SacII digest
Insert: Construct1 PspOMI-SacII digest
Construct4: pBSIISK+DTA-Cdkal1(2856-8800)-loxP-Cdkal1(8801-9800)-FRT-Neor-FRT-loxP-Cdkal1(9801-12500)

(Introduction into Mouse ES Cells and Screening of Recombinant Cells)

The resulting targeting vector was linearized, and the linearized vector was introduced into mouse ES cells by electroporation. Then, from the ES cells carrying a resistance to G418 (neomycin), the ES cells were selected, in which the endogenous gene is replaced by the foreign Cdkal1 gene carried in the targeting vector by homologous recombination. In this process, ES cells derived from C57BL6 were used as mouse ES cells.

(Production of Chimeric Mice)

After screening of the ES cells in the manner as described immediately above, the resulting ES cells were injected into the blastocyst of a mouse (C57BL6), and the resulting blastocyst was returned to the womb of a foster mother mouse, thereby producing chimeric mice.

(Production of Type 2 Diabetes Model Non-Human Mammalian Animal (Mouse))

Using the chimeric mice as produced above, the model non-human mammalian animals for type 2 diabetes were produced. The verification of the genomic type and so on of each mouse was carried out by collecting tissue from the tail, etc. of each mouse, purifying DNA, and carrying out PCR.

The resulting chimeric mice were crossed with wild type mice to give heterozygotic mice (Cdkal$1^{flox/+,neomycin/+}$).

The resulting heterozygotic mice (Cdkal$1^{flox/+,neomycin/+}$) was then crossed with FLP-expressing mice to produce heterozytotic mice with the neomycin gene removed therefrom (Cdkal$1^{flox/+}$).

Then, the resulting heterozygotic mice (Cdkal$1^{flox/+}$) were crossed with each other to produce homozygotic mice (Cdkal$1^{flox/flox}$).

Thereafter, the resulting homozygotic mice (Cdkal$1^{flox/flox}$) were further crossed with RIP-Cre mice carrying a Cre recombinase gene with a rat insulin promoter sequence to produce heterozygotic mice (Cdkal$1^{flox/+,RIP-Cre/O}$) carrying a RIP-Cre gene. In a working embodiment of the present invention, the heterozygotic mice (Cdkal$1^{flox/+,RIP-Cre/O}$) can play a role as a non-human mammalian animal in which it is inserted at a site downstream of a promoter of a gene expressing specifically in the pancreas.

The heterozygotic mice (Cdkal$1^{flox/+,RIP-Cre/O}$) were further crossed with the homozygotic mice (Cdkalflox/flox) Here, the homozygotic mice (Cdkal$1^{flox/flox}$) play a role as a non-human animal having a site-specific recombination enzyme recognition sequence in the 3'-untranslated region and the 5'-untranslated region of the particular domain carrying one exon or more exons of the Cdkal1 gene.

The crossing of the heterozygotic mice) ($^{Cdkal1flox/+,RIP-Cre/O}$) with the homozygotic mice (Cdkal$1^{flox/flox}$) produced Cdkal1 gene-deficient mice (Cdkal$1^{flox/flox,RIP-Cre/O}$) as the non-human mammalian animal model for type 2 diabetes deficient in a Cdkal1 gene function specifically on the chromosome of the β cells of the pancreas.

The resulting non-human mammalian animal model for type 2 diabetes (mice) (they may also be referred to hereinafter as "knock-out mice") and the wild type mice were used for verification of time-course changes in the body weight and the blood glucose level.

(Verification of Time-Course Changes of Body Weight)

Using male mice (4 wild type mice and 6 knock-out mice) and female mice (9 wild type mice and 7 knock-out mice), time-course changes of the body weight during a period of from 3-week-old to 7-week-old were measured. The results are indicated in FIG. 3A and FIG. 3B.

Figure 3B:
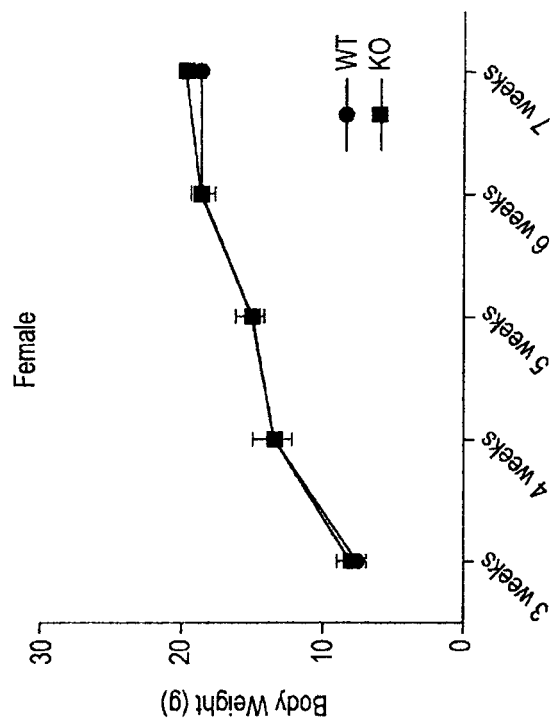
FIG. 3B An illustration showing the time-course changes of the body weight of female mice during a period of from 3-week-old to 7-week-old.
Figure 3A:
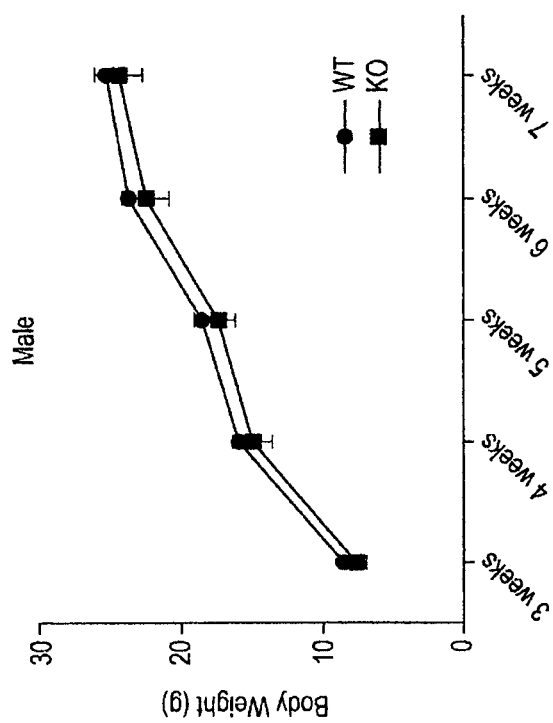
FIG. 3A An illustration showing the time-course changes of the body weight of male mice during a period of from 3-week-old to 7-week-old.

As shown in FIG. 3A and FIG. 3B, no remarkable difference in periodical changes in the body weight was recognized between the wild type mice and the knock-out mice in male or female mice. No significant difference was also recognized in the significance verification by the two-way repeated measure ANOVA. This means that no increase in body weight characteristic for type 2 diabetes was recognized.

(Verification of Periodical Variations in Blood Glucose Level)

Using 5-week-old male mice (4 wild type mice and 6 knock-out mice) and female mice (9 wild type mice and 7 knock-out mice), periodical changes in the blood glucose level were verified.

The test was carried out by intraperitoneal administration of 1 g of glucose solution (0.1 gram/ml) per kilogram of body weight to each mouse abstained from food overnight, and collecting blood immediately after administration up to 90 minutes thereafter to measure a change in the blood glucose level. The results are shown in FIG. 4A and FIG. 4B.

Figure 4B:
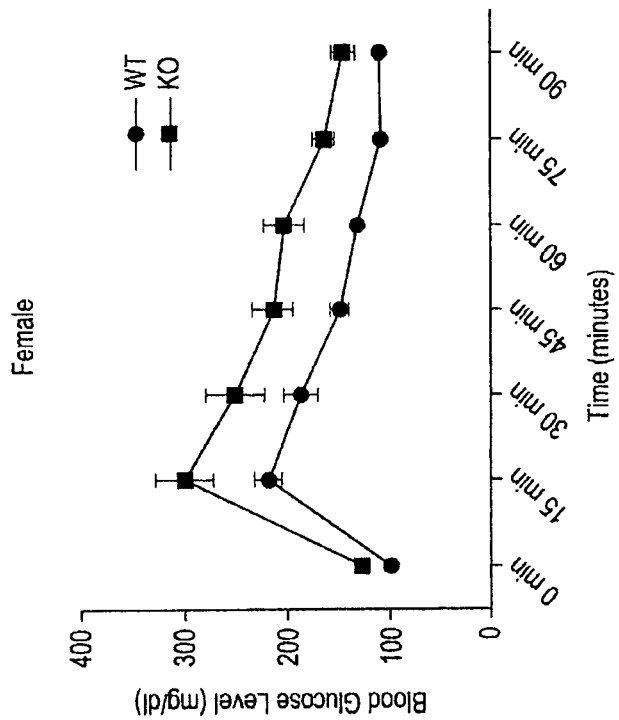
FIG. 4B An illustration showing the periodical changes in the blood glucose level of female wild type and knock-out mice after intraperitoneal administration of 1 g of glucose solution (0.1 gram/ml) per kilogram of body weight.
Figure 4A:
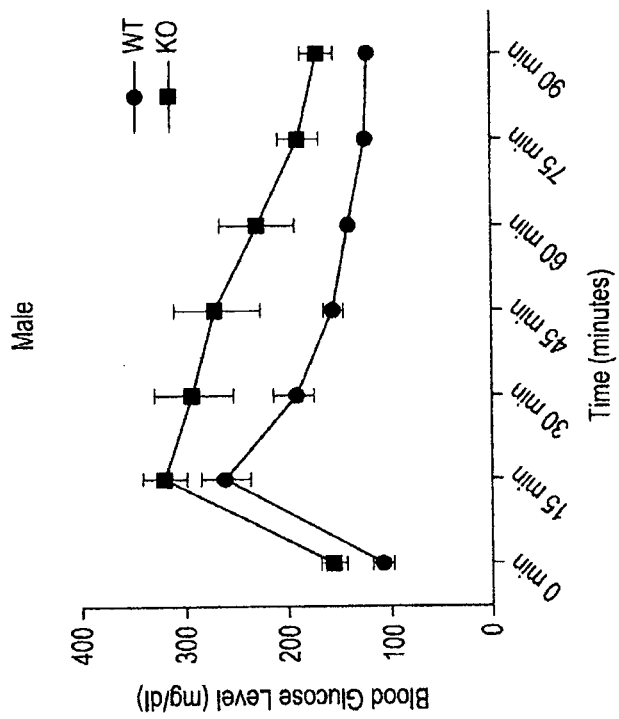
FIG. 4A An illustration showing the periodical changes in the blood glucose level of male wild type and knock-out mice after intraperitoneal administration of 1 g of glucose solution (0.1 gram/ml) per kilogram of body weight.

As shown in FIG. 4A and FIG. 4B, there was a significant difference in the blood glucose level after glucose challenge between the wild type mice and the knock-out mice. These results demonstrate that the blood glucose level decreased significantly slower in the knock-out mice, whether they are male or female, than the wild type mice.

A significance test carried out by two-way repeated measure ANOVA revealed a significant difference between the wild type mice and knock-out mice (male mice: $p<0.01$; female mice: $p<0.0001$). This indicates that the characteristic pathological conditions for type 2 diabetes were observed in the knock-out mice in such a manner that no increase in body weight was recognized but a state of high blood glucose was sustained.

(Verification of Changes of Body Weight Upon Feeding a High Fat Diet)

Changes of body weight were measured by feeding each of the knock-out mice (KO) and the wild type mice (WT) a high fat diet (HFD) containing fat at a rate of 45% of the total calories or a low fat diet (LFD) containing fat at a rate of 10% of the total calories for nine weeks. The results are shown in FIG. 5.

Figure 5:
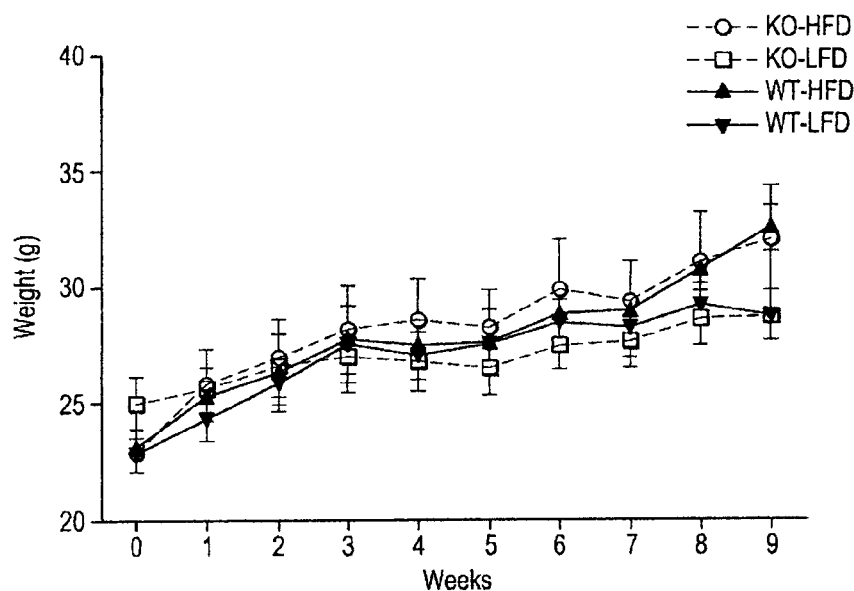
FIG. 5 An illustration showing the changes of body weight of wild type and knock-out mice upon feeding a high fat diet.

As shown in FIG. 5, no remarkable difference in body weight was recognized between the KO mice fed with a high fat diet and the WT mice fed with a high fat diet. A significance test using ANOVA did not reveal any significant difference between them.

(Verification of Periodical Variations of Blood Glucose Level After Feeding a High Fat Diet for Three Weeks)

Figure 6:
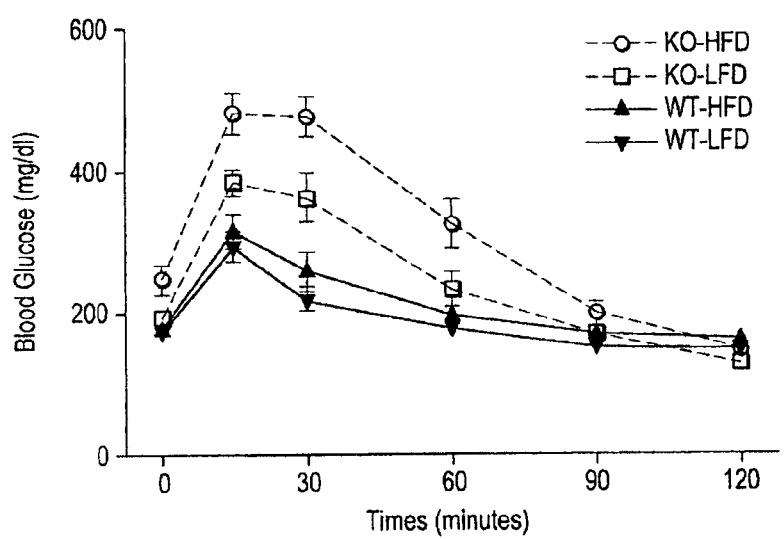
FIG. 6 An illustration showing the periodical changes of blood glucose level after feeding a high fat diet for three weeks.

After KO mice and WT mice were fasted for 7 hours from 8:00 am, they were challenged by intraperitoneal administration of glucose. Blood was collected periodically from the tail, and the blood glucose levels were measured. The results are shown in FIG. 6.

The significance test using ANOVA revealed that the KO mice with a high fat diet fed for three weeks demonstrated a significantly higher peak value of the blood glucose level than any other mouse of the experimental groups. On the other hand, the WT mice with a high fat diet fed for three weeks did not demonstrate any significant difference of variations in the blood glucose level from the WT mice fed with a low fat diet. This indicates that the KO mice fed with a high fat diet demonstrated typical pathological conditions of type 2 diabetes such that no increase in body weight was recognized but a control of the blood glucose level was worsened by feeding a high fat diet.

(Verification of Periodical Changes of Blood Glucose Level After Feeding a High Fat Diet for Nine Weeks)

Figure 7:
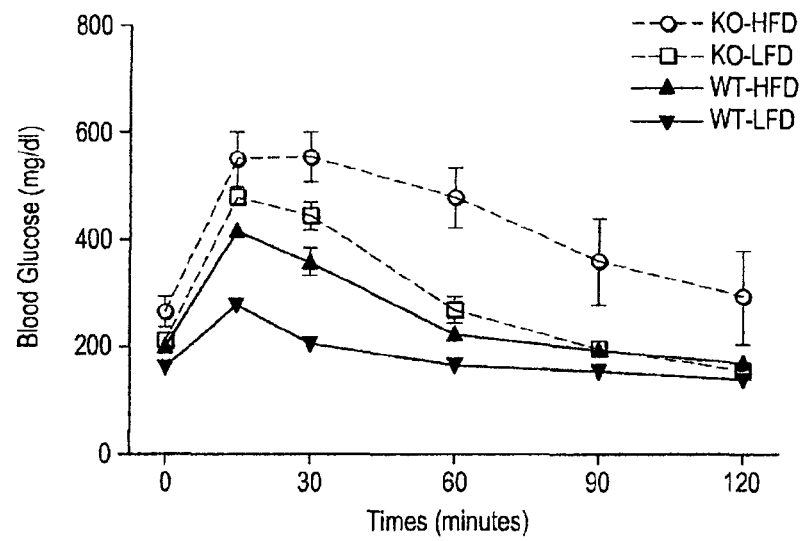
FIG. 7 An illustration showing the periodical changes of blood glucose level after feeding a high fat diet for nine weeks.

After KO mice and WT mice were fasted for 7 hours from 8:00 am, they were challenged by intraperitoneal administration of glucose at a rate of 1 gram glucose per kilogram of body weight. Blood was then collected periodically from the tail, and the blood glucose level was measured. The results are shown in FIG. 7.

The KO mice with a high fat diet fed for nine weeks were shown to be remarkably higher in blood glucose level after 2 hours as well as at the peak time than the WT mice fed with a high fat diet or a low fat diet. This reveals that the KO mice fed with a high fat diet for 9 weeks demonstrated a worsening of a pathological condition of the type 2 diabetes by the long-time feeding of a high fat diet.

(Verification of Periodical Variations in Blood Insulin Values After Feeding a High Fat Diet for 8 Weeks)

Figure 8:
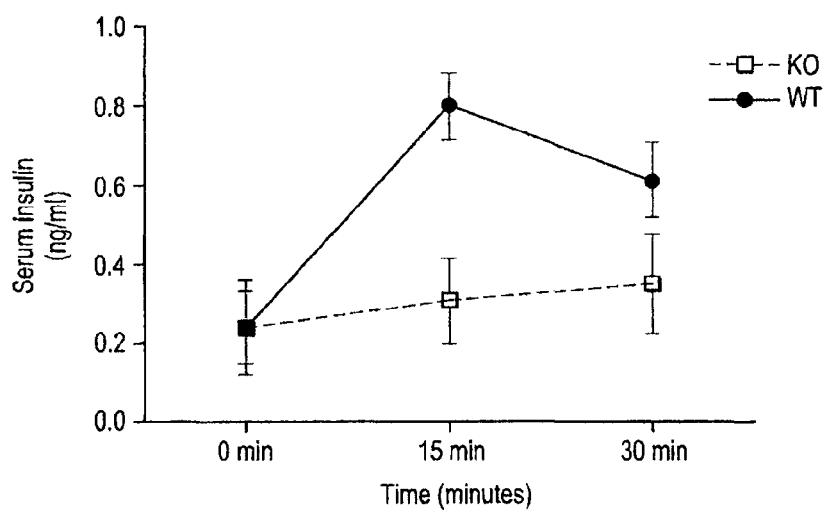
FIG. 8 An illustration showing the periodical changes of blood insulin values after feeding a high fat diet for eight weeks.

After the KO mice were fed a high fat diet or the WT mice were fed a high fat diet, they were fasted for 7 hours after 8:00 am, followed by intraperitoneal administration of glucose at a rate of 1 gram glucose per kilogram of body weight. Blood was collected periodically from the tail, and the blood insulin value was measured by ELISA method. The results are shown in FIG. 8.

The KO mice fed with a high fat diet showed a significant decrease in the insulin secretion after administration of insulin compared with the WT mice ($p<0.05$). This indicates that the KO mice fed with a high fat diet demonstrated a pathological condition typical of type 2 diabetes in such a manner that the ability of secreting insulin was decreased.

(Verification of Fasting Blood Glucose Level After Feeding a High Fat Diet for 3 Weeks)

Figure 9:
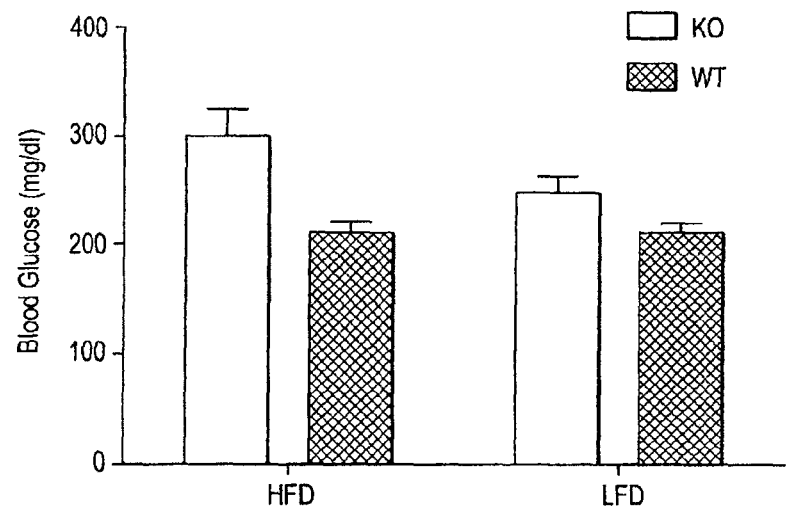
FIG. 9 An illustration showing the fasting blood glucose level after feeding a high fat diet for three weeks.

After fasting mice for 7 hours from 8:00 am at the point of time when they were fed a high fat diet or a low fat diet for three weeks, blood was collected from the tail and the fasting blood glucose level was measured. The results are shown in FIG. 9.

The KO mice fed with a high fat diet demonstrated a significantly higher fasting blood glucose level than the WT mice fed with a high fat diet. On the other hand, the KO mice fed with a low fat diet did not demonstrate a difference in fasting blood glucose level from the WT mice. This indicates that the KO mice fed with a high fat diet demonstrated a pathological condition typical of type 2 diabetes in such a manner that the fasting blood glucose level was elevated.

(Verification of Progressive Blood Glucose Level After Feeding a High Fat Diet for 3 Weeks)

Figure 10:
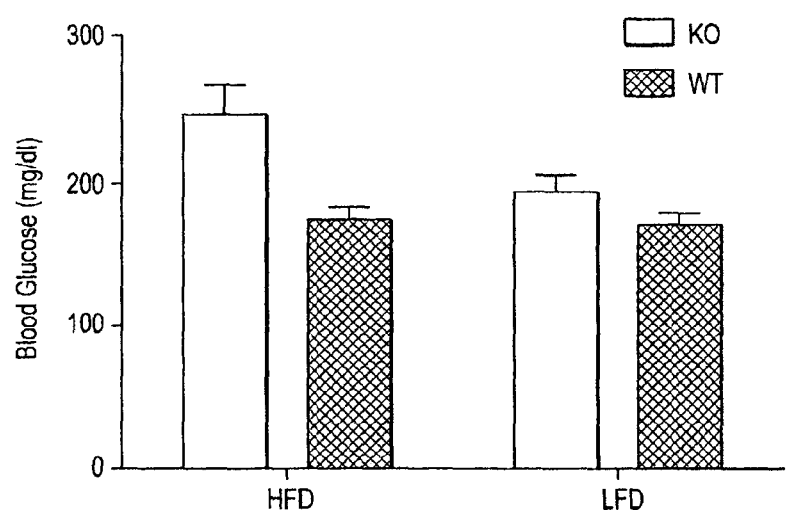
FIG. 10 An illustration showing the progressive blood glucose level after feeding a high fat diet for three weeks.

After mice were fed a high fat diet or a low fat diet for 3 hours, blood was collected from each tail at 10 a.m., and non-fasting blood glucose level was measured. The results are shown in FIG. 10.

The KO mice fed with a high fat diet demonstrated a significantly higher progressive blood glucose level than the WT mice fed with a high fat diet. On the other hand, the KO mice fed with a low fat diet did not show a difference from the WT mice. This indicates that the KO mice fed with a high fat diet demonstrated a pathological condition of type 2 diabetes such that the non-fasting blood glucose level was elevated.

(Verification of Insulin Susceptibility After Feeding a High Fat Diet for 8 Weeks)

Figure 11:
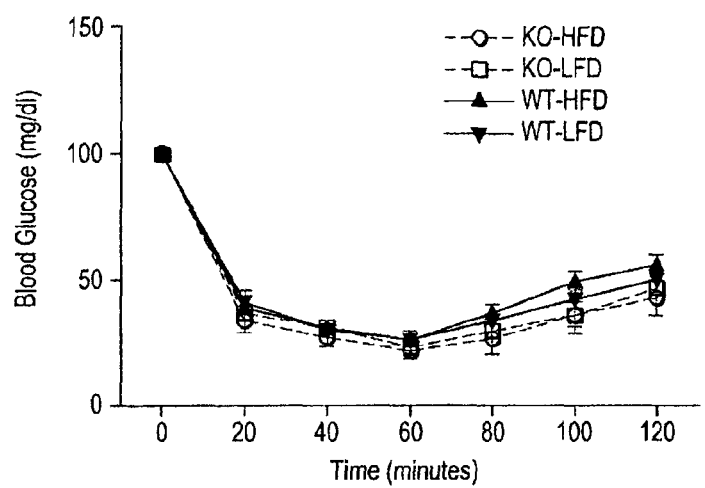
FIG. 11 An illustration showing the insulin susceptibility after feeding a high fat diet for eight weeks.

After KO mice or WT mice fed with a high fat diet were intraperitoneally administrated each with insulin at a rate of 1 U/kg of body weight, and blood was collected periodically from each tail, followed by measuring the blood glucose level. The results are shown in FIG. 11.

No difference of a degree of a decrease in blood glucose level by insulin administration was recognized among all experimental groups. This indicates that the KO mice fed with a high fat diet demonstrated a pathological condition of type 2 diabetes by hyposecretion of insulin, not a pathological condition of type 2 diabetes having insulin resistance.

(Screening of a Preventive or Therapeutic Agent for Type 2 Diabetes Resulting from Abnormality of Cdkal1)

To the KO mice used for the verification of periodical changes of blood glucose level, Exendin-4 which is an agonist of a glucagon-like peptide-1 receptor known as a therapeutic agent for type 2 diabetes was intraperitoneally administrated as a test substance. A degree of type 2 diabetes was then evaluated using the KO mice to simulate the screening of the preventive or therapeutic agent for type 2 diabetes caused by the Cdkal1 abnormality.

The procedures for evaluating the degree of type 2 diabetes consists of measuring the fasting blood glucose level and glucose-tolerance blood glucose level for KO mice and WT mice, comparing the blood glucose levels for both of the mice, and evaluating them. In this test, Exendin-4 was administered twice a day for 2 weeks at a rate of 0.1 mg per kg, of body weight. The results are shown in FIG. 12.

Figure 12:
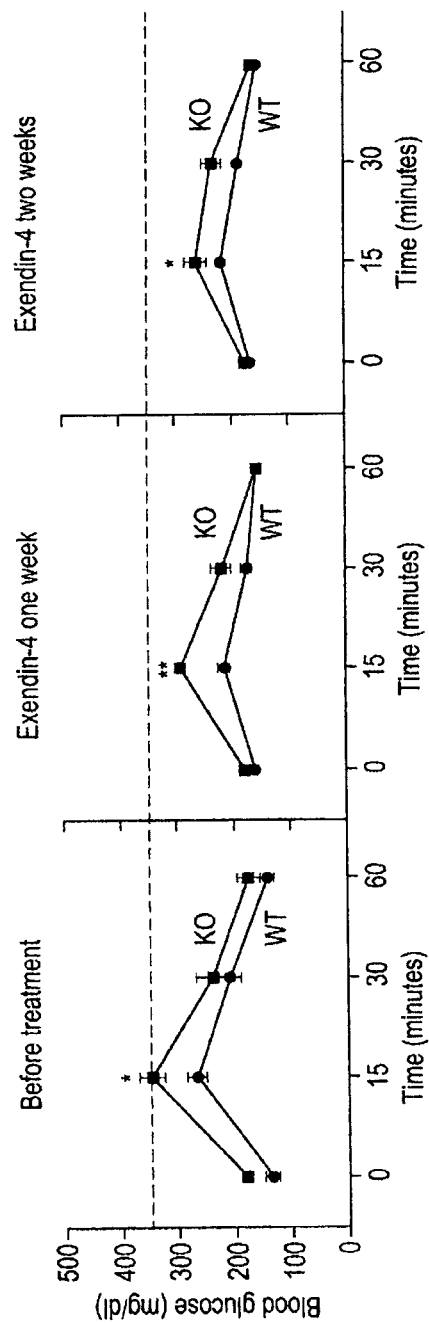
FIG. 12 An illustration showing the fasting blood glucose level and glucose-tolerance blood glucose level for wild type and knock-out mice before and after administration of Exendin-4.

As shown in FIG. 12, the KO mice demonstrated significantly higher blood glucose levels in 15 minutes after glucose tolerance before and after administration of Exendin-4 than the WT mice (*$p<0.05$, **$p<0.01$). On the other hand, the results of administration of Exendin-4 after 1 week and 2 weeks showed that both of the KO mice and the WT mice demonstrated a significantly improved glucose tolerance by administration of Exendin-4 (verification by ANOVA: $p=0.02$).

The above results showed an improved glucose tolerance by administration of Exendin-4 to the non-human mammalian animal model for type 2 diabetes according to the present invention.

The above test results implies that the administration of an unknown test substance to the type 2 diabetes non-human mammalian animal model according to the present invention can provide the possibility of screening the preventive or therapeutic agent for type 2 diabetes.

As described above, the non-human mammalian animal model for type 2 diabetes according to the present invention can provide a new model non-human mammalian animals for type 2 diabetes, which develop spontaneously a pathological condition similar to that of the type 2 diabetes of a non-obese type popular for the Japanese people because the non-human mammalian animals according to the present invention are the one that is deficient specifically in a Cdkal1 gene function on the chromosome of the β cells of the pancreas.

Moreover, as the non-human mammalian animal model for type 2 diabetes according to the present invention knocked its Cdkal1 gene out specifically in the pancreas, there is no risk that the Cdkal1 gene is caused to be expressed in any organ other than the pancreas, thereby adversely exerting an influence on any other organ. Therefore, in the event that the type 2 diabetes non-human mammalian animal model according to the present invention is used for tests or experiments, more accurate test or experimental results can be expected to be obtained compared with wild type non-human mammalian animals as a control because no attention is needed to be paid to the expression of the Cdkal1 gene at the site other than the pancreas.

The non-human mammalian animal model for type 2 diabetes according to the present invention can be expected to contribute to more accurate research on the type 2 diabetes and the screening of the preventive or therapeutic agent for type 2 diabetes because they were different from those developing type 2 diabetes, which were produced by interbreeding wild mice as disclosed in Japanese patent publication #2006-034,132.

In conclusion, a description regarding each embodiment of the present invention as described above is made solely for an illustrative purpose. Therefore, any embodiment not described above is construed as being encompassed within the scope of the present invention as far as it does not deviate from the technical concept of the present invention, and various modifications therefrom are made feasible in accordance with designs of the present invention.

The invention claimed is:

1. A transgenic mouse whose genome comprises a homozygous inactivation of the CDK5 regulatory subunit associated protein 1-like 1 (Cdkal1) gene in cells of the pancreas such that no Cdkal1 protein is produced in said cells, wherein said transgenic mouse after being fed a high fat diet containing fat at an amount of 45% of the total calories for three weeks exhibits a phenotype, wherein said phenotype comprises a higher blood glucose level and a lower level of insulin secretion when compared to a wild type mouse fed said high fat diet, or when compared with said wild type mouse fed a low fat diet, or said transgenic mouse fed a low fat diet, wherein said low fat diet contains fat at an amount of 10% of the total calories.

2. A transgenic mouse whose genome comprises a homozygous inactivation of the Cdkal1 gene in cells of the pancreas such that no Cdkal1 protein is produced in said cells, wherein said transgenic mouse is produced by a method comprising:
interbreeding a first mouse whose genome comprises at least exon 5 of the Cdkal1 gene flanked by the same orientation of recognition sites for a site-specific recombination enzyme, with a second mouse whose genome comprises a site-specific recombination enzyme transgene, wherein said enzyme is expressed from a pancreas-specific promoter and is capable of recognizing said recognition sites and catalyzing recombination between said recognition sites in cells of the pancreas to produce said transgenic mouse,
wherein said transgenic mouse after being fed a high fat diet containing fat at an amount of 45% of the total calories for three weeks exhibits a phenotype, wherein said phenotype comprises a higher blood glucose level and a lower level of insulin secretion when compared to a wild type mouse fed said high fat diet, or when compared with said wild type mouse fed a low fat diet, or said transgenic mouse fed a low fat diet, wherein said low fat diet contains fat at an amount of 10% of the total calories.

3. A transgenic mouse whose genome comprises a homozygous inactivation of the Cdkal1 gene in cells of the pancreas such that no Cdkal1 protein is produced in said cells, wherein said gene consists of a deletion in exon 5, wherein said cells are deficient in promoting translation of insulin and in modifying tRNA, wherein said transgenic mouse after being fed a high fat diet containing fat at an amount of 45% of the total calories for three weeks exhibits a phenotype, wherein said phenotype comprises a higher blood glucose level and a lower level of insulin secretion when compared to a wild type mouse fed said high fat diet, or when compared with said wild type mouse fed a low fat diet, or said transgenic mouse fed a low fat diet, wherein said low fat diet contains fat at an amount of 10% of the total calories.

4. A transgenic mouse whose genome comprises a homozygous inactivation of the Cdkal1 gene in cells of the pancreas such that no Cdkal1 protein is produced in said cells, wherein said gene consists of a deletion in exon 5, wherein said cells are deficient in promoting translation of insulin and in modifying tRNA, wherein said transgenic mouse is produced by a method comprising:

interbreeding a first mouse whose genome comprises exon 5 of the Cdkal1 gene flanked by the same orientation of recognition sites for a site-specific recombination enzyme, with a second mouse whose genome comprises a site-specific recombination enzyme transgene, wherein said enzyme is expressed from a pancreas-specific promoter and is capable of recognizing said recognition sites and catalyzing recombination between said recognition sites in cells of the pancreas to produce said transgenic mouse, wherein said transgenic mouse after being fed a high fat diet containing fat at an amount of 45% of the total calories for three weeks exhibits a phenotype, wherein said phenotype comprises a higher blood glucose level and a lower level of insulin secretion when compared to a wild type mouse fed said high fat diet, or when compared with said wild type mouse fed a low fat diet, or said transgenic mouse fed a low fat diet, wherein said low fat diet contains fat at an amount of 10% of the total calories.

5. A transgenic mouse whose genome comprises a homozygous inactivation of the Cdkal1 gene in cells of the pancreas such that no Cdkal1 protein is produced in said cells, wherein said gene comprises a deletion in exon 5, wherein said transgenic mouse is deficient in a function of Cdkal1 gene in cells of the pancreas, or wherein said cells are deficient in promoting translation of insulin, and wherein said transgenic mouse is produced by a method comprising:

interbreeding a first mouse whose genome comprises exon 5 of the Cdkal1 gene flanked by the same orientation of recognition sites for a site-specific recombination enzyme, with a second mouse whose genome comprises a site-specific recombination enzyme transgene, wherein said enzyme is expressed from a pancreas-specific promoter and is capable of recognizing said recognition sites and catalyzing recombination between said recognition sites in cells of the pancreas to produce said transgenic mouse, wherein said transgenic mouse after being fed a high fat diet containing fat at an amount of 45% of the total calories for three weeks exhibits a phenotype, wherein said phenotype comprises a higher blood glucose level and a lower level of insulin secretion when compared to a wild type mouse fed said high fat diet, or when compared with said wild type mouse fed a low fat diet, or said transgenic mouse fed a low fat diet, wherein said low fat diet contains fat at an amount of 10% of the total calories.

6. The transgenic mouse according to claim 5, wherein said mouse lacks only exon 5 of the Cdkal1 gene.

7. The transgenic mouse according to claim 1, wherein a weight of said transgenic mouse after being fed a high fat diet containing fat at an amount of 45% of the total calories for three weeks is not significantly greater than the weight of a wild type mouse after being fed said high fat diet for three weeks.

\* \* \* \* \*

SEQUENCE LISTING

```
<160> NUMBER OF SEQ ID NOS: 8

<210> SEQ ID NO 1
<211> LENGTH: 5945
<212> TYPE: DNA
<213> ORGANISM: Mus musculus
<220> FEATURE:
<221> NAME/KEY: misc_feature
<222> LOCATION: (2626)..(2795)
<223> OTHER INFORMATION: Cdkal1 fragment with Exon4 (2856-8800)

<400> SEQUENCE: 1
gggccctttt gtcagtccca cctcctttct ttggtaagaa aataattttt agaaaactcc      60
taaggtcagc ggatgttcag tttctttcct gcacttcttc acactccaag cctgtgcatt     120
tagatctgaa agaggaagaa tttcctgaat gtgttcaaac tgttattttt tttttttcac     180
tgacagatat tgcatgtaaa tggaacctat gtgggaaagg ccaatcttaa tggctgagct     240
ggtaaaccct tgtttctagg aggcgaatgc ccaatccaaa agatgttaga ctccagaggg     300
agggtagtgg ctccggtgag tgagccgagt acggttgcac ctcaggtgct caatgcagtc     360
attatgtctg catctcttgc taggcttcat tccttaggta ggtggcttct ttggcctgtc     420
acagatttca ccaagttggc ctattacccc aacttcatgc actggagtgg aaagagaagc     480
tgtctttact gtcagttgtt gtaaaggtct tttctggctg gatcgtcttg ttgtgactga     540
ctctgagcaa atcactgtct aggaaaagga aggaaggagc gactgactgg gatgtgctca     600
ttaccataac agtttttagg atgggtgctt ggctcacttt ttttttttctt ttactgatga     660 tagatatata agtggctgag atttaaatag aggtttgaat tatgatgcac acgctgttaa     720
agatttaaag caaacattgc aaattccagg cacaaaaata ggcctggtag gaagccactc     780
tgttatttgg atgatgtgag cagaaagatg ggaatcctat agaagaacaa aaagggagct     840
tatcagacag gcttgaagac acatgactat atagcagtgg gtcgcaacct tcctaatgct     900
gcaacccttt aatacagttc ctcatggtgt ggtgacccat aaccttaaaa ttacttttag     960
tgctacttca taaactgtaa atttgctatt gttatgaatt gtaatgtaaa taactgtggt    1020
ttttgatggt cttaggtgac ccccgtgaag ttatttgcac cccccaaag gggtcatgac    1080 ctacaggttg agaactgctg atttatagtc ttcacactgg ttcagataac ctaatgagga    1140
```

```
aagttaatag gtaatagatg ccatagtatg catgggccta gactctttct ttactgccag    1200
cttcaacccc aattcattac ttctttcttt gaggttattt tattttatat atatgaatat    1260
tttgcatgca tgtacatatg tgcaccacat acatgcctgg tacctttgag gttcagaaaa    1320
gggtatcaga ttctctggaa ctggaatcat agatggtatt gagtcaccat gtgggtgctg    1380
ggaacagaac ccaggtcctc tgctagagcc acaggctttc ttatctgcta aaccatctct    1440
ctatcccctt ctctaagact tttatcatta tggcatgttg gattttgtca aaggcatcta    1500
ttgagatgat catgaggttt ttttcatctt taagttcatt tatgtcattt attggcttaa    1560
tatatgctga actatctcta catctctggg atacagttaa tttaatgttt ttgatataga    1620
cctacctgtg tttggtttgt aaacatttta ttcatgatta taacattagt gtttaccagg    1680
ggtattagct ggtagttttc tttttcttc tttcttttt ttttttttta atgtgtgtgc    1740
ctttatttgg ttttgatatt agagtaatac tttgtagttg tttaccaata ctagttttga    1800
ttggcatagc tgtcctatgt gtgtgtgtgt gtgtgtgt gtgtgtgt gtgcatgcat    1860 gactcaccat attatatgta tatgagcgtt tttgcctgta tgtatttatg tgcaccaaaa    1920
atgtgcctgg tgcccaagga ggtcagaagg tgccagatcc cttgaactgg acttatgatg    1980
gtattgagcc tctgtgtggg tactggaact gaacgatgga cttctataaa atcagcaagt    2040
tctcttatct gctgagccat ctcttgagcc ccaccaatca ctcttttttt tgtttgtttg    2100 ttttttgtt tttttgtttt gttttcgag acagggtttc tctgtatagc cttggctatc    2160
ctggagctca ctttgtagac caggctggcc tcgaactcag aaatccgcct gcctctgcct    2220
ccggagtgct gggattaaag gtgtgcgcca ccaccgccca gccccaccaa tcactcttaa    2280
agtcaggtat accaattcct tctcacagta ctggaggcct tggtggtcac tggcctcagc    2340
agcagtggct gatgggaatt gctggctttc tgtttccttt ctcttgaaaa gaccctgccc    2400
tactttctct ccatagtatt agttatgaca ttttcagttc agtcatgggt gttctatata    2460
tgcaggactt gcatggttgt ttcttttggtt tatctatgtt ttctgtggac ttaggtttca    2520
cagagttaag aagattcaag gttggtaaga attgttgacc aataccatgc taagtggatt    2580
tttataaacc tctgctattt gtaacttttt tctgtcctac aaaagatgcc ttctgcgtct    2640
tgtgatgtac tgctggatga catagaagat atcatatcac aggaagattc aaagccacag    2700
gacagacagt tctcaagaaa gcatgtgttt cctaaagtac gaaggcggaa tacccaaaaa    2760
tatttgcaag aagagcccag gccaccaagt gacaggtaag cattcctcag aattacattc    2820
acttccgtcc cagaagaggc tggcactgct ggcctacact gtatgtgcag taactccagg    2880
tataggatct ttgtatttct agtaggaaac atagagctta aaaaaaaaa aaaaaaaaa    2940 aaaggaattg cttcaaatct ggccagtaat aggttaaaaa ctcagaaatt tctaattctt    3000
cataccaagg gcatggggaa ttaggggaac ggatatgatc aaattacatt gaagagaatt    3060
ttccaagaat taattaaaaa caaaacaaaa taccagttta aatgttcttt gaaggaaggt    3120
gataggacac taggagttgt tttgatttga ctatagttgg tataaatctg ttgtaattgc    3180
agattaaagc tttgaatcct ctgtggcagt gggtgttttg gacgtgtgat tattgttagc    3240
atattagtga gtgcttaggg atcacacaca aggcactggg cacaaagacc attgtcctgt    3300 ctgcccttt gtggtgggat tctagacagt aagagtgtag taggacactg cagaggtgat    3360
tgcctagctg tccatagcct gtgactgttc acctagtaaa tggtgggcag ctctcatgtt    3420
ggctttgttt agatgattga gcttttcagg gctctgcatg gagaaggtgg ttttttattt    3480
```

```
ttatttatt   attttattag   atattttctt   catttacatt   tcaaatgcta   tccccaaagt   3540
cccctatacc  ctcctcccgc   cctggtagaa   ggtgttttaa   ttagtggagt   ttgtcacatt   3600
tatttcaagc  atgtctttat   tgtcatttct   gtttactttt   aagttgttag   gacagtctaa   3660
gaggagagtc  tttttgtcct   tccgagataa   attctctaga   aacctgtgac   tggagttaca   3720
tgaattatgg  agttttcaag   tttggttatt   tttaatctgt   aaattttaag   tggataaaga   3780
ttgcaactag  tatttaagag   tttgtgaatg   acagttcat   cagcctttgt   ttttatttat   3840
ttatttattt  ttattatttt   attttctgag   acagggtttc   tctgtgtagc   cctggctgtc   3900
ctggaactca  ctttgtagac   caggctggcc   tcgaactcag   aaatccgcct   gcctctgcct   3960
cccaagtgct  gggattaaag   gcgtgcgcca   ccactgcctg   gctgttttta   ttcttaatat   4020
gttttctgtg  ttgtatactc   tgtaaatgtt   catgagagtg   aacaggtacc   tgtgtgtgtg   4080
tgtgtgtgtg  tgtgtgtgtg   tgtgtgtgtg   tgtgtgtgtg   tacactacag   gtcagattag   4140
gtatcttcct  tgattgcttt   ccaccttatt   tcttgggaca   gggacaggga   cagggactgt   4200
cactgaagct  ggagctgttg   attctgctag   ggtggctgcc   tgtttgttct   agggattctt   4260
ctgtcttctc  cctgacaggc   actggggttg   catatgcctg   ctgctccacc   tgactttttt   4320
tctgggtgct  gggtgtccag   tacccccagg   tcatatcctc   atacttatag   ggtagtactt   4380
tatggcatca  ccgtctcctc   agcccttctt   gttttgggtg   ctacagctgc   cattttcggt   4440
gtgaccgttt  tgtgtatct    ttctaaaagc   tgcatcagtc   attggtggta   tggtgagtag   4500
ggattaaaac  tacaatccag   agaagacctt   tttctgaggc   aagatctctt   gtagcttggt   4560
ccacagatga  ccctgaactt   cctgcttctc   tttcctaagt   gctgggatta   cagttgtgtg   4620
ccacctggct  tgaaaggaca   ttttaaaat    taaaatttgt   atttaaaatg   tttttcaaaa   4680
atgacatctt  atttacttag   gatgtatgag   caggcatgag   cgcgtgctga   agcacgtgag   4740
tgagggtcag  aagtcagctt   aggagtcggt   tctctaacgt   ggatctcggg   gttggactca   4800
ggtcatcagg  cgtgggggca   ggctccgtga   cctgctaagc   cttctcatgg   atccaaaagg   4860
acgttattta  tttacttcta   acatcatttt   caccttctat   tgaagataga   ttttgttcaa   4920
cataattttc  tgattatgat   ctctccttcc   tctactcctc   ccagctccta   tccatctccc   4980
ctcccatcca  gatccacccc   ttttctgtct   ctctcagaaa   acaaacagaa   taaaataaaa   5040
tgtaataaga  gaaacagaa    aggcattgac   ctatgactat   agtgtcaatt   tattgctaca   5100
tttgtttggt  tttaccctag   tgtctggcct   atccagtctg   gcccaacatt   gttggggatg   5160
tgttctgtct  catggagtgg   gccataaatc   caatcagata   ttagctggca   tgtctcacaa   5220
gccttatgct  actgttgcac   tagtgcagtg   attctctgtc   ttcctaataa   tgtgacccct   5280
taatacagtt  ccttatgttg   tggtgacccct   caactataga   attactgcat   tgctacttca   5340
taactgtaat  tctgttatag   ctatgaattg   taatgtaaat   atctgacatg   ggggatatgc   5400
agcctccgaa  ggggtcatga   ctggtgggtt   gagaagctcc   gaagcactgc   actagtgcat   5460
ctggtatgga  ggtcaccatt   gtagtctgaa   gagtttgcag   ctgggttagt   atttaccctc   5520
tcctctagta  gtctgcagag   tacatttcag   tactgtgacc   atttagtcag   tagtggtgaa   5580
ggctcttggt  aggcaacaac   tgcacttctc   catgttcagt   gagatgtgta   ggtgttgtct   5640
ttagcagtag  ggccttacca   taagcgtatg   gagagcaatc   ttatcaacag   cctgggttgt   5700
tttggggttc  ccatgggacc   cttagaccaa   caactcagtt   agaggtaatc   tatttctagt   5760
cctggcattt  ggtgacaaaa   gacacaaaag   gacattgtat   aaagacagag   agccttcttg   5820
tgactccttg  gttatttat    ccggatttta   gttttaaaac   actttgctta   ttattgtgtc   5880
```

```
tgtatgcaga atgtgtttaa gtcttaggta gggttttat ttctgcaatg aaacaccatg    5940
accaa                                                                5945
```

<210> SEQ ID NO 2
<211> LENGTH: 1000
<212> TYPE: DNA
<213> ORGANISM: Mus musculus
<220> FEATURE:
<221> NAME/KEY: misc_feature
<222> LOCATION: (449)..(561)
<223> OTHER INFORMATION: Cdkal1 fragment with Exon5 (8801-9800)

<400> SEQUENCE: 2

```
aaagcacgct gggaggagag gggattatac agcttacact tactttcaca gcactttctt     60
cattgaagga cgtcaggaca ggaactcaaa tggcagcttc attgaggtag aagctgatgc    120
agaagtcatg gaaggattct gctaactggc ttgctcccag tggcttgctc agccttcttt    180
cttatagaac ccaggaccac cagcccaggg atggtaccac cacgatgagc tgggtgacaa    240
gtgcatttac tcgcccatct agctcactga cccttatttt agagttttgt tgcaacggca    300
gattttaaaa tagtttggtg cattctgtaa ctagattgtg aattgattcg tttgttttt    360 tgtgtaatgt gccctaaaat catcgagtgg cttttatctt aagaatcact tacagatact    420
cactttgttc taattgatta cttaacagca ctattccagg catacagaaa atttggatcc    480
gaacatgggg ctgctcacat aataattcgg atggagaata catggctgga cagcttgctg    540
cctatggcta taaaattaca ggtaatgaga tccataatgt attttattga ttatatttca    600
gagttgcaga ttttggagac aggtagtcta gccccagcag tttaagggaa ttttagagta    660
atttaatgat aggaaggtag agcactaata gcgactatat attattagat aactggttac    720
atctttcttg acttctattg tatttctgtt tgtttatatt acattttatt tgtgtgtgta    780
tatgcagggt ggagggtggg gagggacac acatgcacag tggtacacat gtggaggtca    840
ggagacagct gcaggagaag agacctctct cctgtgtggg atcttggggc aggcttgacg    900
acaggtgcct ttgcccactg agccatctca cctgcctggt tattttaaaa taaccttaaa    960
accttttgta ttttgaagtg aaactgcagg aaattcatgt                          1000
```

<210> SEQ ID NO 3
<211> LENGTH: 34
<212> TYPE: DNA
<213> ORGANISM: Bacteriophage P1
<220> FEATURE:
<221> NAME/KEY: misc_feature
<223> OTHER INFORMATION: loxP sequence

<400> SEQUENCE: 3

```
ataacttcgt atagcataca ttatacgaag ttat                                 34
```

<210> SEQ ID NO 4
<211> LENGTH: 2700
<212> TYPE: DNA
<213> ORGANISM: Mus musculus
<220> FEATURE:
<221> NAME/KEY: misc_feature
<223> OTHER INFORMATION: Cdkal1 fragment (9801-12500)

<400> SEQUENCE: 4

```
aaggccaaag gagggcatta gctgtttgga gtaacagtca gtgagagctg cttcgtgggt     60
atcaggactt aaactggggt cctctggaag agcaccatgg tttgaaatgt tgagacatat    120
```

```
atctagtccc actttttagca attttttattc taatttttta tgatacttta ttttatgtat    180
agtggtacaa tttatacact gaataacata agaggatgat tatatgtatt tttttggtca    240
gagtttaact ttgtagttct ggctggtctg gatcttgtta tgtcaactgg ttggccttga    300
actcacagca ttgatccttc tgcctctctt gggattaaga catataccac catgaccagt    360
ctagcttcat atttactgtg cgtatgtgca cttccgtggg ctctggagat ccggactgtt    420
agcttgtgga ggaagtactt tataccctga gacgtctcca cagccctcct tgttgtcttt    480
tttaacactg tggagttcgc agagtcttta cctctgctaa acatatcctt tgttttgagc    540
tgtatttccc caactctctg tagacctcaa gttgagacct gaaacataat ttgcatggtt    600
tctggattac tgatattagg tgttttggtt attgtggatt agtgggattg tgttaatatt    660
attaatttaa attgttttg ttaattaagt atgggcctaa aatatcaatg aatataacat    720
aggtgtaaaa tttagatttc atgtactgaa tacagggatt attggaaaga agttaagatt    780
tcttaatagc tacttgtagc cattttacta tttggtgaag aaacatgatt tgggtaaaga    840
tacttgaaat tgctgtctgt aactccgagt ctgatacatg ataattctgc aggaaaacgt    900
aagatttgga gtgaaggaaa agattcatcg tttaaaaaaa tattgctctg agacagggat    960
tcagagtccc caagtagctg aggatggctt gcgtttctgc tcctccgtgt ggtttggtgc    1020
tgggccggaa cccagggcag gggtgtgcta ggcaggcagg caggcaggcc accttcggag    1080
gagagcccat ggagatgggt ggtgttttcc tagcaaacgt cacacagaac aattagtatc    1140
aagaagagtg ggagatgata gaattaaatg ggcaaggtgg caagtaggtg aactttcttc    1200
atgggaacta gtgttttaa aaggaatatg ttgtggctga gctggcaggt gcacttgggg    1260
aactgaggca ggaggactgt gagttgtagg tagctgctgt gtagtgggac actgtctcag    1320
aagcaagtgg agacgtgatg tgaacacctg catcccagga gcatcctcca ggaagcaggc    1380
tgaaggctga cctctgccct aggaaggctc tgttgctgtt tctgttgaag agcttgccaa    1440
attatctcca gtgtcttcat ttgtgggaaa ctgtcgtgtc ttctcacatg aagtgttata    1500
aacaagcgac ctgtgggtaa gatttgggc atgctagtga ataatgctgt tctagttaac    1560
agtagacatt tcatcttta ttttttctta ctctatagcc caggctggcc ttaaactcac    1620
aggaacactc ctgcctagtg agtactggga ttttttggtag ttacatttct gtttgtcata    1680
attggttctg ggaactcttg aagagtagca gcaattcttg tttatttatt gattttaaca    1740
tactgcctca ctgtctcttt cctctgtgag gaccaggctg gcctcagctc atagagcagc    1800
agtacttcgt atgctttctg ggtctcttca gactccctca taatacagtt ctatcaaaaa    1860
actcattaca actgggtacg tagttctagt aaaatatgag cctggcttcc ctaggtgggt    1920
cccgcattca caacagttat gctaatgtgt agttatacct gttgctcatg ggtattgcat    1980
gtgcatgatg gtttgtggga aagtccgccc ccggttgagt tctcataggc acatgagggg    2040
actgtgtgct tgtggaccat cttatggaag tcagaactga gtctttatct tgggtgtcct    2100
agttgcagaa agcgtaaaca tctctaggct gttacattct tgatggttcc tttgtatctt    2160
tgtatatagc ttaatcagtt ggcaagtatg ttgtgagcat actgtgtatt cgtgggtaga    2220
gttctaggaa cttgtggaga cacaaaagga agaatcttta tattgcttaa atcttagagg    2280
ttgtcttggg caatgcttat ttctaatgga ttcttgcttt ctcttttaat aatagagaaa    2340
agtaggatct gctgtagtta aaactttta taatctgtat tttagaaata ctgtagcatt    2400
ttgtgtttga tttgaggaac tctctcgtgt agggagacag cacagtggac tgactcaggt    2460
gtatagcgta ctcctgggct ttggccactc aatgcgaagt atctttaact tgtgtgcctg    2520
```

| | | | | |
|---|---|---|---|---|
| aggtcagttt | catgtatttg | attcatgtat | ggagaatttt | atataggaaa tgcatacaag | 2580 |
| gatcacatta | ctgattaggt | tattaaaatg | aaattttag | tttgtgttga tgttgacaga | 2640 |
| agtaatgctt | gttacataaa | gttacttaaa | aaccgcagtg | acagcaaatg ttgcctggtt | 2700 |

<210> SEQ ID NO 5
<211> LENGTH: 1516
<212> TYPE: DNA
<213> ORGANISM: Transposon Tn5
<220> FEATURE:
<221> NAME/KEY: misc_feature
<223> OTHER INFORMATION: Neomycine resistance gene

<400> SEQUENCE: 5

| | | | | |
|---|---|---|---|---|
| cgcgccgcac | acaaaaacca | acacacagat | catgaaaata | aagctctttt attggtaccg | 60 |
| aattcgccag | ggagctctca | gacgtcgctt | ggtcggtctt | tattcgaacc ccagagtccc | 120 |
| gctcagaaga | actcgtcaag | aaggcgatag | aaggcgatgc | gctgcgaatc gggagcggcg | 180 |
| ataccgtaaa | gcacgaggaa | gcggtcagcc | cattcgccgc | caagctcttc agcaatatca | 240 |
| cgggtagcca | acgctatgtc | ctgatagcgg | tccgccacac | ccagccggcc acagtcgatg | 300 |
| aatccagaaa | agcggccatt | ttccaccatg | atattcggca | agcaggcatc gccatgggtc | 360 |
| acgacgagat | cctcgccgtc | gggcatgcgc | gccttgagcc | tggcgaacag ttcggctggc | 420 |
| gcgagcccct | gatgctcttc | gtccagatca | tcctgatcga | caagaccggc ttccatccga | 480 |
| gtacgtgctc | gctcgatgcg | atgtttcgct | tggtggtcga | atgggcaggt agccggatca | 540 |
| agcgtatgca | gccgccgcat | tgcatcagcc | atgatggata | ctttctcggc aggagcaagg | 600 |
| tgagatgaca | ggagatcctg | ccccggcact | tcgcccaata | gcagccagtc ccttcccgct | 660 |
| tcagtgacaa | cgtcgagcac | agctgcgcaa | ggaacgcccg | tcgtggccag ccacgatagc | 720 |
| cgcgctgcct | cgtcctgcag | ttcattcagg | gcaccggaca | ggtcggtctt gacaaaaaga | 780 |
| accgggcgcc | cctgcgctga | cagccggaac | acggcggcat | cagagcagcc gatcgtctgt | 840 |
| tgtgcccagt | catagccgaa | tagcctctcc | acccaagcgg | ccggagaacc tgcgtgcaat | 900 |
| ccatcttgtt | caatgccga | tcccatggtt | tagttcctca | ccttgtcgta ttatactatg | 960 |
| ccgatatact | atgccgatga | ttaattgtca | acacgtgctg | ctgcaggtcg aaaggcccgg | 1020 |
| agatgaggaa | gaggagaaca | gcgcggcaga | cgtgcgcttt | tgaagcgtgc agaatgccgg | 1080 |
| gcctccggag | gaccttcggg | cgcccgcccc | gcccctgagc | ccgcccctga gccgcccccc | 1140 |
| ggacccaccc | cttcccagcc | tctgagccca | gaaagcgaag | gagcaaagct gctattggcc | 1200 |
| gctgcccaa | aggcctaccc | gcttccattg | ctcagcggtg | ctgtccatct gcacgagact | 1260 |
| agtgagacgt | gctacttcca | tttgtcacgt | cctgcacgac | gcgagctgcg gggcgggggg | 1320 |
| gaacttcctg | actaggggag | gagtggaagg | tggcgcgaag | gggccaccaa agaacggagc | 1380 |
| cggttggcgc | ctaccggtgg | atgtggaatg | tgtgcgaggc | cagaggccac ttgtgtagcg | 1440 |
| ccaagtgccc | agcggggctg | ctaaagcgca | tgctccagac | tgccttggga aaagcgcctc | 1500 |
| ccctacccgg | tagaat | | | | 1516 |

<210> SEQ ID NO 6
<211> LENGTH: 34
<212> TYPE: DNA
<213> ORGANISM: saccharomyces cerevisiae
<220> FEATURE:
<221> NAME/KEY: misc_feature
<223> OTHER INFORMATION: FRT sequence

```
<400> SEQUENCE: 6
gaagttccta tactttctag agaataggaa cttc                                       34

<210> SEQ ID NO 7
<211> LENGTH: 1478
<212> TYPE: DNA
<213> ORGANISM: Corynebacterium diphteriae
<220> FEATURE:
<221> NAME/KEY: misc_feature
<223> OTHER INFORMATION: diphteria toxin A chain (DTA) gene

<400> SEQUENCE: 7
taccgggtag gggaggcgct tttcccaagg cagtctggag catgcgcttt agcagccccg           60
ctgggcactt ggcgctacac aagtggcctc tggcctcgca cacattccac atccaccggt          120
aggcgccaac cggctccgtt ctttggtggc cccttcgcgc caccttctac tcctcccta           180 gtcaggaagt ccccccccgc cccgcagctc gcgtcgtgca ggacgtgaca aatggaagta          240
gcacgtctca ctagtctcgt gcagatggac agcaccgctg agcaatggaa gcgggtaggc          300
ctttggggca gcggccaata gcagctttgc tccttcgctt tctgggctca gaggctggga          360
aggggtgggt ccggggcgg gctcagggc gggctcaggg gcgggcggg cgcccgaagg             420 tcctccggag gcccggcatt ctgcacgctt caaaagcgca cgtctgccgc gctgttctcc          480
tcttcctcat ctccgggcct ttcgacctaa gcttgccacc atggatcctg atgatgttgt          540
tgattcttct aaatcttttg tgatggaaaa cttttcttcg taccacggga ctaaacctgg          600
ttatgtagat tccattccaa aaggtataca aagccaaaa tctggtacac aaggaaatta          660
tgacgatgat tggaaagggt tttatagtac cgacaataaa tacgacgctg cgggatactc          720
tgtagataat gaaaacccgc tctctggaaa agctggaggc gtggtcaaag tgacgtatcc          780
aggactgacg aaggttctcg cactaaaagt ggataatgcc gaaactatta agaaagagtt          840
aggtttaagt ctcactgaac cgttgatgga gcagtcgga acggaagagt ttatcaaaag          900
gttcggtgat ggtgcttcgc gtgtagtgct cagccttccc ttcgctgagg ggagttctag          960
cgttgaatat attaataact gggaacaggc gaaagcgtta agcgtagaac ttgagattaa         1020
ttttgaaacc cgtggaaaac gtggccaaga tgcgatgtat gagtatatgg ctcaagcctg         1080
tgcaggaaat cgtgtcaggc gatctctttg tgaaggaacc ttacttctgt ggtgtgacat         1140
aattggacaa actacctaca gagatttaaa gctctaaggg gatccgctgt aagtctgcag         1200
aaattgatga tctattaaac aataaagatg tccactaaaa tggaagtttt tcctgtcata         1260
ctttgttaag aagggtgaga acagagtacc tacattttga atggaaggat tggagctacg         1320 gggtgggg tgggtggga ttagataaat gcctgctctt tactgaaggc tctttactat           1380
tgctttatga taatgtttca tagttggata tcataattta aacaagcaaa accaaattaa         1440
gggccagctc attcctccca ctcatgatct atagatcc                                 1478

<210> SEQ ID NO 8
<211> LENGTH: 15822
<212> TYPE: DNA
<213> ORGANISM: Artificial
<220> FEATURE:
<223> OTHER INFORMATION: artificial
<220> FEATURE:
<221> NAME/KEY: misc_feature
<223> OTHER INFORMATION: Targeting Vector

<400> SEQUENCE: 8
ctaaattgta agcgttaata ttttgttaaa attcgcgtta aatttttgtt aaatcagctc           60
```

```
atttttaac caataggccg aaatcggcaa atcccttat aaatcaaaag aatagaccga      120
gatagggttg agtgttgttc cagtttggaa caagagtcca ctattaaaga acgtggactc    180
caacgtcaaa gggcgaaaaa ccgtctatca gggcgatggc ccactacgtg aaccatcacc   240
ctaatcaagt tttttggggt cgaggtgccg taaagcacta aatcggaacc ctaaagggag   300 ccccgatt agagcttgac ggggaaagcc ggcgaacgtg gcgagaaagg aagggaagaa    360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcggc ctcttcgcta ttacgccagc tggcgaaagg    540
gggatgtgct gcaaggcgat taagttgggt aacgccaggg ttttcccagt cacgacgttg   600
taaaacgacg ccagtgagc gcgcgtaata cgactcacta tagggcgaat tgggtaccgg    660
gccgctctag aactagtgga tcccccgggc tgcaggaatt ctaccgggta ggggaggcgc   720
ttttcccaag gcagtctgga gcatgcgctt tagcagcccc gctgggcact ggcgctaca    780 caagtggcct ctggcctcgc acacattcca catccaccgg taggcgccaa ccggctccgt   840
tctttggtgg ccccttcgcg ccaccttcta ctcctcccct agtcaggaag ttccccccg    900 ccccgcagct cgcgtcgtgc aggacgtgac aaatggaagt agcacgtctc actagtctcg   960
tgcagatgga cagcaccgct gagcaatgga agcgggtagg cctttggggc agcggccaat   1020
agcagctttg ctccttcgct ttctgggctc agaggctggg aaggggtggg tccggggcg    1080 ggctcagggg cgggctcagg ggcggggcgg gcgcccgaag gtcctccgga ggcccggcat   1140
tctgcacgct tcaaaagcgc acgtctgccg cgctgttctc ctcttcctca tctccgggcc   1200
tttcgaccta agcttgccac catggatcct gatgatgttg ttgattcttc taaatctttt   1260
gtgatggaaa acttttcttc gtaccacggg actaaacctg gttatgtaga ttccattcaa   1320
aaaggtatac aaaagccaaa atctggtaca caaggaaatt atgacgatga ttggaaaggg   1380
ttttatagta ccgacaataa atacgacgct gcgggatact ctgtagataa tgaaaacccg   1440
ctctctggaa aagctggagg cgtggtcaaa gtgacgtatc caggactgac gaaggttctc   1500
gcactaaaag tggataatgc cgaaactatt aagaaagagt taggtttaag tctcactgaa   1560
ccgttgatgg agcaagtcgg aacggaagag tttatcaaaa ggttcggtga tggtgcttcg   1620
cgtgtagtgc tcagccttcc cttcgctgag gggagttcta gcgttgaata tattaataac   1680
tgggaacagg cgaaagcgtt aagcgtagaa cttgagatta ttttgaaaac ccgtggaaaa   1740
cgtggccaag atgcgatgta tgagtatatg gctcaagcct gtgcaggaaa tcgtgtcagg   1800
cgatctcttt gtgaaggaac cttacttctg tggtgtgaca taattggaca aactacctac   1860
agagatttaa agctctaagg ggatccgctg taagtctgca gaaattgatg atctattaaa   1920
caataaagat gtccactaaa atggaagttt ttcctgtcat actttgttaa gaagggtgag   1980
aacagagtac ctcatttg aatgaagga ttggagctac ggggggtgggg gtggggtggg     2040 attagataaa tgcctgctct ttactgaagg ctctttacta ttgctttatg ataatgtttc   2100
atagttggat atcataattt aaacaagcaa aaccaaatta agggccagct cattcctccc   2160
actcatgatc tatagatccc tcgagggggg gccctttgt cagtcccacc tccttctttt    2220
ggtaagaaaa taattttag aaaactccta aggtcagcgg atgttcagtt tctttcctgc    2280
acttcttcac actccaagcc tgtgcattta gatctgaaag aggaagaatt tcctgaatgt   2340
gttcaaactg ttatttttt tttttcactg acagatattg catgtaaatg gaacctatgt   2400
```

```
gggaaaggcc aatcttaatg gctgagctgg taaaccttg tttctaggag gcgaatgccc      2460
aatccaaaag atgttagact ccagaggag ggtagtggct ccggtgagtg agccgagtac      2520
ggttgcacct caggtgctca atgcagtcat tatgtctgca tctcttgcta ggcttcattc     2580
cttaggtagg tggcttcttt ggcctgtcac agatttcacc aagttggcct attaccccaa    2640
cttcatgcac tggagtggaa agagaagctg tctttactgt cagttgttgt aaaggtcttt   2700
tctggctgga tcgtcttgtt gtgactgact ctgagcaaat cactgtctag gaaaaggaag    2760
gaaggagcga ctgactggga tgtgctcatt accataacag ttttaggat gggtgcttgg     2820 ctcactttt tttttctttt actgatgata gatatataag tggctgagat ttaaatagag    2880
gtttgaatta tgatgcacac gctgttaaag atttaaagca aacattgcaa attccaggca    2940 caaaatagg cctggtagga agccactctg ttatttggat gatgtgagca gaaagatggg    3000
aatcctatag aagaacaaaa agggagctta tcagacaggc ttgaagacac atgactatat   3060
agcagtgggt cgcaaccttc ctaatgctgc aacccttaa tacagttcct catggtgtgg    3120
tgacccataa ccttaaaatt acttttagtg ctacttcata aactgtaaat ttgctattgt    3180
tatgaattgt aatgtaaata actgtggttt ttgatggtct taggtgaccc ccgtgaagtt   3240
atttgcaccc ccccaaaggg gtcatgacct acaggttgag aactgctgat ttatagtctt    3300
cacactggtt cagataacct aatgaggaaa gttaataggt aatagatgcc atagtatgca   3360
tgggcctaga ctcttctt actgccagct tcaaccccaa ttcattactt ctttctttga      3420
ggttatttta ttttatatat atgaatatt tgcatgcatg tacatatgtg caccacatac     3480
atgcctggta cctttgaggt tcagaaaagg gtatcagatt ctctggaact ggaatcatag    3540
atggtattga gtcaccatgt gggtgctggg aacagaaccc aggtcctctg ctagagccac    3600
aggctttctt atctgctaaa ccatctctct atccccttct ctaagacttt tatcattatg    3660
gcatgttgga ttttgtcaaa ggcatctatt gagatgatca tgaggttttt ttcatcttta    3720
agttcattta tgtcatttat tggcttaata tatgctgaac tatctctaca tctctgggat    3780
acagttaatt taatgttttt gatatagacc tacctgtgtt tggtttgtaa acattttatt    3840
catgattata acattagtgt ttaccagggg tattagctgg tagttttctt tttcttctt    3900 tcttttttt tttttttaat gtgtgtgcct ttatttggtt ttgatattag agtaatactt    3960
tgtagttgtt taccaatact agttttgatt ggcatagctg tcctatgtgt gtgtgtgtgt   4020
gtgtgtgtgt gtgtgtgtgt gcatgcatga ctcaccatat tatatgtata tgagcgtttt   4080
tgcctgtatg tatttatgtg caccaaaaat gtgcctggtg cccaaggagg tcagaaggtg   4140
ccagatccct tgaactggac ttatgatggt attgagcctc tgtgtgggta ctggaactga   4200
acgatggact tctataaaat cagcaagttc tcttatctgc tgagccatct cttgagcccc    4260
accaatcact cttttttttg tttgtttgtt ttttgtttt tttgttttgt tttcgagac       4320 agggtttctc tgtatagcct tggctatcct ggagctcact tgtagacca ggctggcctc    4380 gaactcagaa atccgcctgc ctctgcctcc ggagtgctgg gattaaaggt gtgcgccacc   4440
accgcccagc cccaccaatc actcttaaag tcaggtatac caattccttc tcacagtact    4500
ggaggccttg gtggtcactg gcctcagcag cagtggctga tgggaattgc tggctttctg    4560 tttccttct cttgaaaaga ccctgcccta ctttctctcc atagtattag ttatgacatt     4620
ttcagttcag tcatgggtgt tctatatatg caggacttgc atggttgttt ctttggttta   4680 tctatgttt ctgtggactt aggttcaca gagttaagaa gattcaaggt tggtaagaat     4740
tgttgaccaa taccatgcta agtggatttt tataaacctc tgctatttgt aactttttc    4800
```

```
tgtcctacaa aagatgcctt ctgcgtcttg tgatgtactg ctggatgaca tagaagatat    4860
catatcacag gaagattcaa agccacagga cagacagttc tcaagaaagc atgtgtttcc    4920
taaagtacga aggcggaata cccaaaaata tttgcaagaa gagcccaggc caccaagtga    4980
caggtaagca ttcctcagaa ttacattcac ttccgtccca gaagaggctg gcactgctgg    5040
cctacactgt atgtgcagta actccaggta taggatcttt gtatttctag taggaaacat    5100
agagcttaaa aaaaaaaaaa aaaaaaaaaa aggaattgct tcaaatctgg ccagtaatag    5160
gttaaaaact cagaaatttc taattcttca taccaagggc atggggaatt aggggaacgg    5220
atatgatcaa attacattga agagaatttt ccaagaatta ttaaaaaca aaacaaaata    5280 ccagtttaaa tgttctttga aggaaggtga taggacacta ggagttgttt tgatttgact    5340
atagttggta taaatctgtt gtaattgcag attaaagctt tgaatcctct gtggcagtgg    5400
gtgttttgga cgtgtgatta ttgttagcat attagtgagt gcttagggat cacacacaag    5460
gcactgggca caaagaccat tgtcctgtct gcccttttgt ggtgggattc tagacagtaa    5520
gagtgtagta ggacactgca gaggtgattg cctagctgtc catagcctgt gactgttcac    5580
ctagtaaatg gtgggcagct ctcatgttgg ctttgtttag atgattgagc ttttcagggc    5640
tctgcatgga gaaggtggtt ttttattttt atttatttat tttattagat attttcttca    5700
tttacatttc aaatgctatc cccaaagtcc cctataccct cctcccgccc tggtagaagg    5760
tgttttaatt agtggagttt gtcacattta tttcaagcat gtctttattg tcatttctgt    5820 ttactttaa gttgttagga cagtctaaga ggagagtctt tttgtccttc cgagataaat    5880
tctctagaaa cctgtgactg gagttacatg aattatggag ttttcaagtt tggttatttt    5940
taatctgtaa attttaagtg gataaagatt gcaactagta tttaagagtt tgtgaatgga    6000
cagttcatca gcctttgttt ttatttattt atttattttt atttatttat ttctgagac    6060 agggtttctc tgtgtagccc tggctgtcct ggaactcact tgtagacca ggctggcctc    6120 gaactcagaa atccgcctgc ctctgcctcc caagtgctgg gattaaaggc gtgcgccacc    6180
actgcctggc tgtttttatt cttaatatgt tttctgtgtt gtatactctg taaatgttca    6240
tgagagtgaa caggtacctg tgtgtgtgtg tgtgtgtgtg tgtgtgtgtg tgtgtgtgtg    6300
tgtgtgtgta cactacaggt cagattaggt atcttccttg attgctttcc accttatttc    6360
ttgggacagg gacagggaca gggactgtca ctgaagctgg agctgttgat tctgctaggg    6420
tggctgcctg tttgttctag ggattcttct gtcttctccc tgacaggcac tggggttgca    6480
tatgcctgct gctccacctg acttttttc tgggtgctgg gtgtccagta cccccaggtc    6540
atatcctcat acttataggg tagtacttta tggcatcacc gtctcctcag cccttcttgt    6600
tttgggtgct acagctgcca ttttcggtgt gaccgtttgt gtgtatcttt ctaaaagctg    6660
catcagtcat tggtggtatg gtgagtaggg attaaaacta caatccagag aagacctttt    6720
tctgaggcaa gatctcttgt agcttggtcc acagatgacc ctgaacttcc tgcttctctt    6780
tcctaagtgc tgggattaca gttgtgtgcc acctggcttg aaaggacatt tttaaaatta    6840
aaatttgtat ttaaaatgtt tttcaaaaat gacatcttat ttacttagga tgtatgagca    6900
ggcatgagcg cgtgctgaag cacgtgagtg agggtcagaa gtcagcttag gagtcggttc    6960
tctaacgtgg atctcggggt tggactcagg tcatcaggcg tggggcagg ctccgtgacc    7020 tgctaagcct tctcatggat ccaaaaggac gttatttatt tacttctaac atcattttca    7080
ccttctattg aagatagatt tgttcaaca taattttctg attatgatct ctccttcctc    7140
```

```
tactcctccc agctcctatc catctcccct cccatccaga tccaccccctt ttctgtctct    7200
ctcagaaaac aaacagaata aaataaaatg taataagaga aaacagaaag gcattgacct    7260
atgactatag tgtcaatta ttgctacatt tgtttggttt taccctagtg tctggcctat     7320
ccagtctggc ccaacattgt tggggatgtg ttctgtctca tggagtgggc cataaatcca    7380
atcagatatt agctggcatg tctcacaagc cttatgctac tgttgcacta gtgcagtgat    7440
tctctgtctt cctaataatg tgacccttta atacagttcc ttatgttgtg gtgaccctca    7500
actatagaat tactgcattg ctacttcata actgtaattc tgttatagct atgaattgta    7560
atgtaaatat ctgacatggg ggatatgcag cctccgaagg ggtcatgact ggtgggttga    7620
gaagctccga agcactgcac tagtgcatct ggtatggagg tcaccattgt agtctgaaga    7680
gtttgcagct gggttagtat ttaccctctc ctctagtagt ctgcagagta catttcagta    7740
ctgtgaccat ttagtcagta gtggtgaagg ctcttggtag gcaacaactg cacttctcca    7800
tgttcagtga gatgtgtagg tgttgtcttt agcagtaggg ccttaccata agcgtatgga    7860
gagcaatctt atcaacagcc tgggttgttt tggggttccc atgggaccct tagaccaaca    7920
actcagttag aggtaatcta tttctagtcc tggcatttgg tgacaaaaga cacaaaagga    7980
cattgtataa agacagagag ccttcttgtg actccttggt tattttatcc ggattttagt    8040
tttaaaacac tttgcttatt attgtgtctg tatgcagaat gtgtttaagt cttaggtagg    8100
gttttattt ctgcaatgaa acaccatgac caactcgaga taacttcgta tagcatacat     8160
tatacgaagt tataaagcac gctgggagga gagggggatta tacagcttac acttactttc   8220
acagcacttt cttcattgaa ggacgtcagg acaggaactc aaatggcagc ttcattgagg    8280
tagaagctga tgcagaagtc atggaaggat tctgctaact ggcttgctcc cagtggcttg    8340
ctcagccttc tttcttatag aacccaggac caccagccca gggatggtac caccacgatg    8400
agctgggtga caagtgcatt tactcgccca tctagctcac tgacccttat tttagagttt    8460
tgttgcaacg gcagatttta aaatagtttg gtgcattctg taactagatt gtgaattgat    8520
tcgtttgttt ttttgtgtaa tgtgccctaa aatcatcgag tggcttttat cttaagaatc    8580
acttacagat actcactttg ttctaattga ttacttaaca gcactattcc aggcatacag    8640
aaaatttgga tccgaacatg gggctgctca cataataatt cggatggaga atacatggct    8700
ggacagcttg ctgcctatgg ctataaaatt acaggtaatg agatccataa tgtatttat     8760
tgattatatt tcagagttgc agattttgga gacaggtagt ctagccccag cagtttaagg    8820
gaatttaga gtaatttaat gataggaagg tagagcacta atagcgacta tatattatta    8880
gataactggt tacatctttc ttgacttcta ttgtatttct gtttgtttat attacatttt    8940
atttgtgtgt gtatatgcag ggtggagggg tgggagggga cacacatgca cagtggtaca    9000
catgtggagg tcaggagaca gctgcaggag aagagacctc tctcctgtgt gggatcttgg    9060
ggcaggcttg acgacaggtg cctttgccca ctgagccatc tcacctgcct ggttatttta    9120
aaataacctt aaaaccttt gtattttgaa gtgaaactgc aggaaattca tgtgcggccc      9180
cccctcgagg aagttcctat acttctctaga gaataggaac ttccgcgccg cacacaaaaa   9240
ccaacacaca gatcatgaaa ataaagctct tttattggta ccgaattcgc cagggagctc    9300
tcagacgtcg cttggtcggt ctttattcga accccagagt cccgctcaga agaactcgtc    9360
aagaaggcga tagaaggcga tgcgctgcga atcgggagcg gcgataccgt aaagcacgag    9420
gaagcggtca gcccattcgc cgccaagctc ttcagcaata tcacgggtag ccaacgctat    9480
gtcctgatag cggtccgcca cacccagccg gccacagtcg atgaatccag aaaagcggcc    9540
```

```
attttccacc atgatattcg gcaagcaggc atcgccatgg gtcacgacga gatcctcgcc   9600
gtcgggcatg cgcgccttga gcctggcgaa cagttcggct ggcgcgagcc cctgatgctc   9660
ttcgtccaga tcatcctgat cgacaagacc ggcttccatc cgagtacgtg ctcgctcgat   9720
gcgatgtttc gcttggtggt cgaatgggca ggtagccgga tcaagcgtat gcagccgccg   9780
cattgcatca gccatgatgg atactttctc ggcaggagca aggtgagatg acaggagatc   9840
ctgccccggc acttcgccca atagcagcca gtcccttccc gcttcagtga caacgtcgag   9900
cacagctgcg caaggaacgc ccgtcgtggc cagccacgat agccgcgctg cctcgtcctg   9960
cagttcattc agggcaccgg acaggtcggt cttgacaaaa agaaccgggc gccctgcgc   10020 tgacagccgg aacacggcgg catcagagca gccgatcgtc tgttgtgccc agtcatagcc   10080
gaatagcctc tccacccaag cggccggaga acctgcgtgc aatccatctt gttcaatggc   10140
cgatcccatg gtttagttcc tcaccttgtc gtattatact atgccgatat actatgccga   10200
tgattaattg tcaacacgtg ctgctgcagg tcgaaaggcc cggagatgag gaagaggaga   10260
acagcgcggc agacgtgcgc ttttgaagcg tgcagaatgc cgggcctccg gaggaccttc   10320
gggcgcccgc cccgccccctg agcccgcccc tgagcccgcc cccggaccca cccttccca   10380 gcctctgagc ccagaaagcg aaggagcaaa gctgctattg gccgctgccc caaaggccta   10440
cccgcttcca ttgctcagcg gtgctgtcca tctgcacgag actagtgaga cgtgctactt   10500
ccatttgtca cgtcctgcac gacgcgagct gcgggcggg ggggaacttc ctgactaggg   10560
gaggagtgga aggtggcgcg aagggcccac caaagaacgg agccggttgg cgcctaccgg   10620
tggatgtgga atgtgtgcga ggccagaggc cacttgtgta gcgccaagtg cccagcgggg   10680
ctgctaaagc gcatgctcca gactgccttg ggaaaagcgc ctccctacc cggtagaatg    10740 aagttcctat actttctaga aataggaac ttcgcggccc ggacgtaaac tcctcttcag   10800
acctaataac ttcgtatagc atacattata cgaagttata ttaagggtta ttgaatatga   10860
tcggaattcc tgcagccggg ggatccact agttctagag cggccgcaag gccaaggag    10920 ggcattagct gtttggagta acagtcagtg agagctgctt cgtgggtatc aggacttaaa   10980
ctggggtcct ctggaagagc accatggttt gaaatgttga acatatatc tagtcccact    11040 tttagcaatt tttattctaa ttttttatga tactttattt tatgtatagt ggtacaattt   11100
atacactgaa taacataaga ggatgattat atgtattttt ttggtcagag tttaactttg    11160
tagttctggc tggtctggat cttgttatgt caactggttg gccttgaact cacagcattg    11220
atccttctgc ctctcttggg attaagacat ataccaccat gaccagtcta gcttcatatt    11280
tactgtgcgt atgtgcactt ccgtgggctc tggagatccg gactgttagc ttgtggagga    11340
agtactttat accctgagac gtctccacag ccctccttgt tgtctttttt aacactgtgg    11400
agttcgcaga gtctttacct ctgctaaaca tatcctttgt tttgagctgt atttccccaa   11460
ctctctgtag acctcaagtt gagacctgaa acataatttg catggtttct ggattactga    11520
tattaggtgt tttggttatt gtggattagt gggattgtgt taatattatt aatttaaatt    11580
gtttttgtta attaagtatg ggcctaaaat atcaatgaat ataacatagg tgtaaaattt    11640
agatttcatg tactgaatac agggattatt ggaaagaagt taagatttct taatagctac    11700
ttgtagccat tttactattt ggtgaagaaa catgatttgg gtaaagatac ttgaaattgc    11760
tgtctgtaac tccgagtctg atacatgata attctgcagg aaaacgtaag atttggagtg    11820
aaggaaaaga ttcatcgttt aaaaaaatat tgctctgaga cagggattca gagtccccaa    11880
```

```
gtagctgagg atggcttgcg tttctgctcc tccgtgtggt ttggtgctgg gccggaaccc    11940
agggcagggg tgtgctaggc aggcaggcag gcaggccacc ttcggaggag agcccatgga    12000
gatgggtggt gttttcctag caaacgtcac acagaacaat tagtatcaag aagagtggga    12060
gatgatagaa ttaaatgggc aaggtggcaa gtaggtgaac tttcttcatg ggaactagtg    12120
tttttaaaag gaatatgttg tggctgagct ggcaggtgca cttggggaac tgaggcagga    12180
ggactgtgag ttgtaggtag ctgctgtgta gtgggacact gtctcagaag caagtggaga    12240
cgtgatgtga acacctgcat cccaggagca tcctccagga agcaggctga aggctgacct    12300
ctgccctagg aaggctctgt tgctgtttct gttgaagagc ttgccaaatt atctccagtg    12360
tcttcatttg tgggaaactg tcgtgtcttc tcacatgaag tgttataaac aagcgacctg    12420
tgggtaagat ttggggcatg ctagtgaata atgctgttct agttaacagt agacatttca    12480
tcttttattt tttcttactc tatagcccag gctggcctta aactcacagg aacactcctg    12540
cctagtgagt actgggattt tggtagtta catttctgtt tgtcataatt ggttctggga    12600
actcttgaag agtagcagca attcttgttt atttattgat tttaacatac tgcctcactg    12660
tctctttcct ctgtgaggac caggctggcc tcagctcata gagcagcagt acttcgtatg    12720
ctttctgggt ctcttcagac tccctcataa tacagttcta tcaaaaaact cattacaact    12780
gggtacgtag ttctagtaaa atatgagcct ggcttcccta ggtgggtccc gcattcacaa    12840
cagttatgct aatgtgtagt tatacctgtt gctcatgggt attgcatgtg catgatggtt    12900
tgtgggaaag tccgcccccg gttgagttct cataggcaca tgaggggact gtgtgcttgt    12960
ggaccatctt atggaagtca gaactgagtc tttatcttgg gtgtcctagt tgcagaaagc    13020
gtaaacatct ctaggctgtt acattcttga tggttccttt gtatctttgt atatagctta    13080
atcagttggc aagtatgttg tgagcatact gtgtattcgt gggtagagtt ctaggaactt    13140
gtggagacac aaaaggaaga atctttatat tgcttaaatc ttagaggttg tcttgggcaa    13200
tgcttatttc taatgattc ttgctttctc ttttaataat agagaaaagt aggatctgct    13260
gtagttaaaa acttttataa tctgtatttt agaaatactg tagcattttg tgtttgattt    13320
gaggaactct ctcgtgtagg gagacagcac agtggactga ctcaggtgta tagcgtactc    13380
ctgggctttg gccactcaat gcgaagtatc tttaacttgt gtgcctgagg tcagtttcat    13440
gtatttgatt catgtatgga gaattttata taggaaatgc atacaaggat cacattactg    13500
attaggttat taaaatgaaa tttttagttt gtgttgatgt tgacagaagt aatgcttgtt    13560
acataaagtt acttaaaaac cgcagtgaca gcaaatgttg cctggttccg cggtggagct    13620
ccagcttttg ttccctttag tgagggttaa ttgcgcgctt ggcgtaatca tggtcatagc    13680
tgtttcctgt gtgaaattgt tatccgctca caattccaca caacatacga ccgaaagca    13740
taaagtgtaa agcctggggt gcctaatgag tgagctaact cacattaatt gcgttgcgct    13800
cactgcccgc tttccagtcg ggaaacctgt cgtgccagct gcattaatga atcggccaac    13860
gcgcggggag aggcggtttg cgtattgggc gctcttccgc ttcctcgctc actgactcgc    13920
tgcgctcggt cgttcggctg cggcgagcgg tatcagctca ctcaaaggcg gtaatacggt    13980
tatccacaga atcaggggat aacgcaggaa agaacatgtg agcaaaaggc cagcaaaagg    14040
ccaggaaccg taaaaaggcc gcgttgctgg cgtttttcca taggctccgc cccctgacg     14100
agcatcacaa aaatcgacgc tcaagtcaga ggtggcgaaa cccgacagga ctataaagat    14160
accaggcgtt tccccctgga agctccctcg tgcgctctcc tgttccgacc ctgccgctta    14220
ccggatacct gtccgccttt ctcccttcgg gaagcgtggc gctttctcat agctcacgct    14280
```

```
gtaggtatct cagttcggtg taggtcgttc gctccaagct gggctgtgtg cacgaacccc   14340
ccgttcagcc cgaccgctgc gccttatccg gtaactatcg tcttgagtcc aacccggtaa   14400
gacacgactt atcgccactg gcagcagcca ctggtaacag gattagcaga gcgaggtatg   14460
taggcggtgc tacagagttc ttgaagtggt ggcctaacta cggctacact agaaggacag   14520
tatttggtat ctgcgctctg ctgaagccag ttaccttcgg aaaaagagtt ggtagctctt   14580
gatccggcaa acaaaccacc gctggtagcg gtggttttt tgtttgcaag cagcagatta    14640
cgcgcagaaa aaaaggatct caagaagatc ctttgatctt ttctacgggg tctgacgctc   14700
agtggaacga aaactcacgt taagggattt tggtcatgag attatcaaaa aggatcttca   14760
cctagatcct tttaaattaa aaatgaagtt ttaaatcaat ctaaagtata tatgagtaaa   14820
cttggtctga cagttaccaa tgcttaatca gtgaggcacc tatctcagcg atctgtctat   14880
ttcgttcatc catagttgcc tgactccccg tcgtgtagat aactacgata cgggagggct   14940
taccatctgg ccccagtgct gcaatgatac cgcgagaccc acgctcaccg gctccagatt   15000
tatcagcaat aaaccagcca gccggaaggg ccgagcgcag aagtggtcct gcaactttat   15060
ccgcctccat ccagtctatt aattgttgcc gggaagctag agtaagtagt tcgccagtta   15120
atagtttgcg caacgttgtt gccattgcta caggcatcgt ggtgtcacgc tcgtcgtttg   15180
gtatggcttc attcagctcc ggttcccaac gatcaaggcg agttacatga tcccccatgt   15240
tgtgcaaaaa agcggttagc tccttcggtc ctccgatcgt tgtcagaagt aagttggccg   15300
cagtgttatc actcatggtt atggcagcac tgcataattc tcttactgtc atgccatccg   15360
taagatgctt ttctgtgact ggtgagtact caaccaagtc attctgagaa tagtgtatgc   15420
ggcgaccgag ttgctcttgc ccggcgtcaa tacgggataa taccgcgcca catagcagaa   15480
ctttaaaagt gctcatcatt ggaaaacgtt cttcggggcg aaaactctca aggatcttac   15540
cgctgttgag atccagttcg atgtaaccca ctcgtgcacc caactgatct tcagcatctt   15600
ttactttcac cagcgtttct gggtgagcaa aacaggaag gcaaaatgcc gcaaaaaagg    15660
gaataagggc gacacggaaa tgttgaatac tcatactctt ccttttcaa tattattgaa     15720 gcatttatca gggttattgt ctcatgagcg gatacatatt tgaatgtatt tagaaaaata   15780
aacaaatagg ggttccgcgc acatttcccc gaaaagtgcc ac                       15822
```